(12) United States Patent
Dos Santos et al.

(10) Patent No.: US 7,423,039 B2
(45) Date of Patent: Sep. 9, 2008

(54) (4-PHENYLPIPERAZIN-1-YL)ACYLPIPERIDINE DERIVATIVES, PREPARATION THEREOF AND APPLICATION OF SAME IN THERAPEUTICS

(75) Inventors: Victor Dos Santos, Valergues (FR); Jean Wagnon, Montpellier (FR)

(73) Assignee: Sanofi-aventis, Paris (FR)

( * ) Notice: Subject to any disclaimer, the term of this patent is extended or adjusted under 35 U.S.C. 154(b) by 158 days.

(21) Appl. No.: 11/420,508

(22) Filed: May 26, 2006

(65) Prior Publication Data

US 2007/0021609 A1    Jan. 25, 2007

Related U.S. Application Data

(63) Continuation of application No. PCT/FR04/03067, filed on Nov. 30, 2004.

(30) Foreign Application Priority Data

Dec. 1, 2003    (FR)    ................... 03 14173

(51) Int. Cl.
*A61K 31/496*   (2006.01)
*C07D 211/26*   (2006.01)
*C07D 401/12*   (2006.01)
*C07D 405/12*   (2006.01)
*C07D 409/12*   (2006.01)

(52) U.S. Cl. ............... 514/253.11; 514/253.12; 514/253.13; 544/121; 544/238; 544/295; 544/357; 544/360; 544/364

(58) Field of Classification Search ............ None
See application file for complete search history.

(56) References Cited

U.S. PATENT DOCUMENTS

| | | |
|---|---|---|
| 6,468,990 B1 | 10/2002 | Ross et al. |
| 6,492,380 B1 | 12/2002 | Ross et al. |
| 6,689,797 B2 | 2/2004 | Baroni et al. |
| 7,148,352 B2 | 12/2006 | Ross et al. |
| 2003/0203923 A1 | 10/2003 | Ross et al. |
| 2005/0176722 A1 | 8/2005 | Bono et al. |
| 2006/0063793 A1 | 3/2006 | Ross et al. |
| 2006/0167007 A1 | 7/2006 | Bono et al. |

OTHER PUBLICATIONS

Saragovi et al. Exp. Opin. Ther. Patents, vol. 9(6), pp. 737-751 (1999).*
Allen et al. Clinical Science, vol. 110, pp. 175-191 (2006).*
Schor, Progress in Neurobiology, vol. 77 pp. 201-214 (2005).*
Vippagunta et al. Advanced Drug Delivery Reviews, vol. 48, pp. 3-26 (2001).*

* cited by examiner

*Primary Examiner*—Emily Bernhardt
(74) *Attorney, Agent, or Firm*—Jiang Lin; Raymond S. Parker

(57) ABSTRACT

The invention relates to substituted (4-phenylpiperazin-1-yl) acylpiperidine derivatives of formula (I)

(I)

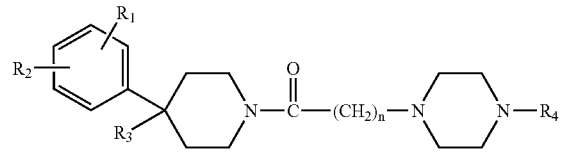

in the form of a base or an addition salt with an acid, and also in the form of a hydrate or solvate, and their preparation process and therapeutic application.

20 Claims, No Drawings

(4-PHENYLPIPERAZIN-1-YL)ACYLPIPERIDINE DERIVATIVES, PREPARATION THEREOF AND APPLICATION OF SAME IN THERAPEUTICS

This application is a Continuation of International Application No. PCT/FR2004/003067, filed Nov. 30, 2004.

FIELD OF THE INVENTION

The present invention relates to substituted (4-phenylpiperazin-1-yl)acylpiperidine derivatives, their preparation and their therapeutic application.

The compounds according to the present invention exhibit affinity for the neurotrophin receptor $p75^{NTR}$.

BACKGROUND OF THE INVENTION

Neurotrophins belong to a family of proteins which possess a similar structure and similar functions and include nerve growth factor (NGF), BDNF (Brain Derived Neurotrophic Factor), neurotrophin-3 (NT-3), neurotrophin-4/5 (NT-4/5) and neurotrophin-6 (NT-6). The biological effects of these proteins (survival and differentiation) are exerted through interaction with membrane receptors having tyrosine kinase activity (trk-A, trk-B and trk-C) (H. THOENEN, Science, 1995, 270, 593-598; G. R. LEWIN and Y. A. BARDE, Annu. Rev. Neurosci., 1996, 19, 289-317; M. V. CHAO, J., Neurobiol., 1994, 25, 1373-1385; M. BOTHWELL, Annu. Rev. Neurosci., 1995, 18, 223-253; G. DECHANT and Y. A. BARDE, Curr. Opin. Neurobiol., 1997, 7, 413-418).

However, many studies show the preponderant role of the $p75^{NTR}$ receptor in the activity of neurotrophins.

The $p75^{NTR}$ receptor, the receptor for all neurotrophins, is a transmembrane glycoprotein of the tumour necrosis factor (TNF) receptor family (W. J. FRIEDMAN and L. A. GREENE, Exp. Cell. Res., 1999, 253, 131-142; J. MELDOSIS et al., Trends Pharmacol. Sci., 2000, 21, 242-243). A number of biological functions are attributed to the $p75^{NTR}$ receptor: on the one hand, the modulation of the affinity of neurotrophins for trk receptors; on the other hand, in the absence of trk, induction of a signal for cell death by apoptosis which occurs through homodimerization of the receptor and activation of the ceramide pathway.

Apoptosis, or programmed cell death, is a physiological mechanism for elimination of cells in numerous tissues. In particular, apoptosis plays a preponderant role in embryogenesis, morphogenesis and cell renewal. Apoptosis is a genetically controlled phenomenon which only occurs at an advanced and irreversible stage of cell lesion.

Many studies show that apoptosis occurs in several pathologies of the central nervous system such as amyotrophic lateral sclerosis, multiple sclerosis, Alzheimer's, Parkinson's and Huntington's diseases and prion diseases. Furthermore, neuronal death through apoptosis also occurs very early after cerebral and cardiac ischaemia. Cell death is also a preponderant phenomenon in atherosclerosis; indeed, the necrosis zones in primary atherosclerotic lesions in humans are evaluated at 80% (M.L. BOCHATON-PIALAT et al., Am. J. Pathol., 1995, 146, 1-6; H. PERLMAN, Circulation, 1997, 95, 981-987). Apoptosis is also involved in mechanisms leading to cell death following cardiac ischaemia-reperfusion (H. YAOITA et al., Cardiovasc. Res., 2000, 45, 630-641).

Several studies show that the $p75^{NTR}$-dependent pro-apoptotic signal is observed in various cell types including neuronal cells, oligodendrocytes, Schwann cells and also hepatic, cardiac and smooth muscle cells (J. M. FRADE et al., Nature, 1996, 383, 166-168; P. LASACCIA-BONNEFIL et al., Nature, 1996, 383, 716-719; M. SOILU-HANNINEN et al., J. Neurosci., 1999, 19, 4828-4838; N. TRIM et al., Am. J. Pathol., 2000, 156, 1235-1243; S. Y. WANG et al., Am. J. Pathol., 2000, 157, 1247-1258). Moreover, a number of experiments carried out in vivo show an increase in the expression of $p75^{NTR}$ following ischaemia in regions of the brain and of the heart in which massive apoptosis is recorded. These results therefore suggest that $p75^{NTR}$ may play a preponderant role in the mechanisms leading to neuronal death through apoptosis post ischaemia (P. P. ROUX et al., J. Neurosci., 1999, 19, 6887-6896; J. A. PARK et al., J. Neurosci., 2000, 20, 9096-9103).

The $p75^{NTR}$ receptor is described as a cellular target for the prion peptide (V. DELLA-BIANCA et al., J. Biol. Chem., 2001, in press) and for the β-amyloid peptide (S. RABIZADEH et al., Proc. Natl. Acad. Sci. USA, 1994, 91, 10703-10706) and would thus be involved in apoptotic phenomena induced by these compounds. These results support the hypothesis according to which $p75^{NTR}$ would play an important role in neuronal death induced by the infectious prion protein (transmissible spongiform encephalopathy) or by the beta-amyloid protein (Alzheimer's disease).

Recent studies suggest that the $p75^{NTR}$ receptor might also play an important role in axonal regeneration, via its function as co-receptor for the Nogo receptor (WONG et al., Nature Neurosci., 2002, 5, 1302-1308; Kerracher and Winton, Neuron, 2002, 36, 345-348). Indeed, several myelin-associated proteins (myelin-associated glycoprotein, MAG, Nogo-A and oligodendrocyte myelin glycoprotein OMgp) inhibit nerve regeneration at the central level during medullary or cranial trauma. These proteins are located in the membrane of the oligodendrocytes directly adjacent to the axon and inhibit neuritic growth by binding with a high affinity to the Nogo receptor located on the axonal membrane. The $p75^{NTR}$ receptor is associated with the Nogo receptor and is involved in the signalling of the inhibitory effects of these myelin proteins in relation to axonal growth. As a result, the $p75^{NTR}$ receptor plays a major role in the regulation of neuronal plasticity and in neuron-glia interactions and represents a therapeutic target of choice for promoting nerve regeneration.

At the peripheral level, recent studies show an increase in the expression of $p75^{NTR}$ and of neurotrophins and a massive apoptosis in atherosclerotic lesions. Furthermore, a pro-angiogenic and vasodilative effect of NGF is also recorded. Finally, a novel form of $p75^{NTR}$ which is truncated in the extracellular part has been identified as well as its major role in established vasculogenesis (D. VON SHACK et al., Nature Neuroscience, 2001, 4, 977-978). All these recent data suggest that $p75^{NTR}$ in its whole or truncated form could also play a preponderant role in vascular pathologies.

A number of compounds are known to interact with the trkA/NGF/$p75^{NTR}$ system or to possess an NGF-type activity. Thus, patent application WO 00/59893 describes substituted pyrimidine derivatives which demonstrate an NGF-type activity and/or which increase the activity of NGF on PC12 cells. Patent applications WO 00/69828 and WO 00/69829 describe polycyclic compounds which inhibit the binding of NGF to the $p75^{NTR}$ receptor in cells which do not express the trkA receptor. Application WO 94/11373 describes pyridazinoquinazolone derivatives which bind to the neurotrophin receptor $p75^{NTR}$. Application WO 94/22866 describes pyrazoloquinazolone derivatives which specifically bind to NGF so as to avoid its attachment to the $p75^{NTR}$ receptor but allowing it to interact with the trk receptor. Application WO 01/49684 describes substituted tetrahydropyridine derivatives which possess activity vis-à-vis the modulation of TNF-alpha.

New (4-phenylpiperazin-1-yl)acylpiperidine derivatives have now been found which exhibit affinity for the receptor $p75^{NTR}$.

SUMMARY OF THE INVENTION

The present invention provides compounds of the formula (I):

(I)

[Structure of formula (I) showing phenyl substituted with $R_1$, $R_2$, $R_3$ attached to a piperidine bearing N—C(O)—(CH$_2$)$_n$—N piperazine N—$R_4$]

in which:
n is 1 or 2;
$R_1$ represents a halogen atom; a trifluoromethyl radical; a $(C_1-C_4)$alkyl; a $(C_1-C_4)$alkoxy; a trifluoromethoxy radical;
$R_2$ represents a hydrogen atom or a halogen atom;
$R_3$ represents a hydrogen atom; a group —OR$_5$; a group —CH$_2$OR$_5$; a group —NR$_6$R$_7$; a group —NR$_8$COR$_9$; a group —CH$_2$NR$_{10}$R$_{11}$; a $(C_1-C_4)$alkoxycarbonyl; a group —CONR$_{12}$R$_{13}$; a —CN radical;
$R_4$ represents a phenyl which is unsubstituted or, mono-, di- or trisubstituted by a substituent selected independently from a halogen atom; a $(C_1-C_4)$alkyl; a $(C_1-C_4)$alkoxy; a trifluoromethyl radical;
$R_5$ represents a hydrogen atom or a $(C_1-C_4)$alkyl;
$R_6$ and $R_7$ represent each independently a hydrogen atom or a $(C_1-C_4)$alkyl;
$R_8$ represents a hydrogen atom or a $(C_1-C_4)$alkyl;
$R_9$ represents a $(C_1-C_4)$alkyl;
$R_{10}$ and $R_{11}$ represent each independently a hydrogen atom or a $(C_1-C_4)$alkyl; $R_{11}$ may also represent a group —CH$_2$R$_{14}$;
or else $R_{10}$ and $R_{11}$, together with the nitrogen atom to which they are attached, constitute a heterocycle selected from aziridine, azetidine, pyrrolidine, piperidine and morpholine;
$R_{12}$ and $R_{13}$ represent each independently a hydrogen atom or a $(C_1-C_4)$alkyl;
or else $R_{12}$ and $R_{13}$, together with the nitrogen atom to which they are attached, constitute a heterocycle selected from azetidine, pyrrolidine, piperidine, morpholine and piperazine which is unsubstituted or substituted in position 4 by a $(C_1-C_4)$alkyl;
$R_{14}$ represents an aromatic group selected from:

[Various heterocyclic aromatic group structures shown]

the said aromatic groups being unsubstituted, mono-substituted or disubstituted by a substituent selected independently from a halogen atom, a $(C_1-C_3)$alkyl or $(C_1-C_3)$alkoxy;
$R_{15}$ represents a hydrogen atom or a $(C_1-C_3)$alkyl.

DETAILED DESCRIPTION OF THE INVENTION

The compounds of formula (I) may exist in the form of bases or addition salts with acids. Such addition salts form part of the invention.

These salts are advantageously prepared with pharmaceutically acceptable acids, although the salts of other acids useful for the purification or isolation of compounds of formula (I) also form part of the invention.

The compounds of formula (I) may also exist in the form of hydrates or solvates, specifically in the form of associations or combinations with one or more molecules of water or with a solvent. Such hydrates and solvates also form part of the invention.

A halogen atom is an atom of bromine, chlorine, fluorine or iodine.

$(C_1-C_3)$Alkyl or $(C_1-C_4)$alkyl respectively is a linear or branched alkyl radical of one to three carbon atoms or one to four carbon atoms, respectively, such as the methyl, ethyl, propyl, isopropyl, butyl, isobutyl, sec-butyl or tert-butyl radical.

$(C_1-C_4)$Alkoxy is a linear or branched alkoxy radical of one to four carbon atoms, such as the methoxy, ethoxy, propoxy, isopropoxy, butoxy, isobutoxy, sec-butoxy or tert-butoxy radical.

Among the compounds of formula (I) provided by the invention mention may be made of the preferred compounds which are defined as follows:
n is 1 or 2;
and/or $R_1$ is in position 3 of the phenyl and represents a trifluoromethyl radical;
and/or $R_2$ represents a hydrogen atom;
and/or $R_3$ represents a hydroxyl, an aminomethyl, a (2-furylmethylamino)methyl, a (2-thienylmethylamino)methyl, a (2-pyridylmethylamino)methyl, a (3-pyridylmethylamino)methyl, a (4-pyridylmethylamino)methyl, a (methylamino)methyl, a (dimethylamino)methyl, an (N-methylethylamino)methyl, a (diethylamino)methyl, an azetidin-1-ylcarbonyl; an aminocarbonyl; an (N-methyl-2-furylmethylamino)methyl; a (3-furylmethylamino)methyl;
and/or $R_4$ represents a phenyl, a 4-chlorophenyl, a 3-chlorophenyl, a 4-fluorophenyl, a 2,4-dichlorophenyl, a 3,4-dichlorophenyl, a 3,5-dichlorophenyl, a 4-methylphenyl, a 2,4-dimethylphenyl, a 3,4-dimethylphenyl, a 3-methoxyphenyl, a 4-methoxyphenyl, a 2,4-dimethoxyphenyl, a 3,4-dimethoxyphenyl, a 3-(trifluoromethyl) phenyl; a 2,3-dimethylphenyl.

Among these last preferred compounds particular preference is given to the compounds of formula (I) for which:

n is 1 or 2;

$R_1$ is in position 3 of the phenyl and represents a trifluoromethyl radical;

$R_2$ represents a hydrogen atom;

$R_3$ represents a hydroxyl, an aminomethyl, a (2-furylmethylamino)methyl, a (2-thienylmethylamino)methyl, a (2-pyridylmethylamino)methyl, a (3-pyridylmethylamino)methyl, a (4-pyridylmethylamino)methyl, a (methylamino)methyl, a (dimethylamino)methyl, an (N-methylethylamino)methyl, a (diethylamino)methyl, an azetidin-1-ylcarbonyl; an aminocarbonyl; an (N-methyl-2-furylmethylamino)methyl; a (3-furylmethylamino)methyl;

$R_4$ represents a phenyl, a 4-chlorophenyl, a 3-chlorophenyl, a 4-fluorophenyl, a 2,4-dichlorophenyl, a 3,4-dichlorophenyl, a 3,5-dichlorophenyl, a 4-methylphenyl, a 2,4-dimethylphenyl, a 3,4-dimethylphenyl, a 3-methoxyphenyl, a 4-methoxyphenyl, a 2,4-dimethoxyphenyl, a 3,4-dimethoxyphenyl, a 3-(trifluoromethyl) phenyl; a 2,3-dimethylphenyl;

in the form of a base or an addition salt with an acid, and in the form of a hydrate or solvate.

Among the compounds of formula (I) provided by the invention particular mention may be made of the following compounds:

4-[3-(trifluoromethyl)phenyl]-1-[[4-[3-(trifluoromethyl) phenyl]piperazin-1-yl]acetyl]piperidin-4-ol;

1-[[4-(3,4-dimethylphenyl)piperazin-1-yl]acetyl]-4-[3-(trifluoromethyl)phenyl]piperidin-4-ol;

1-[[4-(3,5-dichlorophenyl)piperazin-1-yl]acetyl]-4-[3-(trifluoromethyl)phenyl]piperidin-4-ol;

1-[[4-(4-methylphenyl)piperazin-1-yl]acetyl]-4-[3-(trifluoromethyl)phenyl]piperidin-4-ol;

[[1-[(4-phenylpiperazin-1-yl)acetyl]-4-[3-(trifluoromethyl)phenyl]piperidin-4-yl]methyl]amine;

(2-furylmethyl)[[1-[(4-phenylpiperazin-1-yl)acetyl]-4-[3-(trifluoromethyl)phenyl]piperidin-4-yl]methyl]amine;

[[1-(4-phenylpiperazin-1-yl)acetyl]-4-[3-(trifluoromethyl)phenyl]piperidin-4-yl]methyl](2-thienylmethyl) amine;

[[1-(4-phenylpiperazin-1-yl)acetyl]-4-[3-(trifluoromethyl)phenyl]piperidin-4-yl]methyl](pyrid-2-ylmethyl) amine;

[[1-(4-phenylpiperazin-1-yl)acetyl]-4-[3-(trifluoromethyl)phenyl]piperidin-4-yl]methyl](pyrid-3-ylmethyl) amine;

[[1-(4-phenylpiperazin-1-yl)acetyl]-4-[3-(trifluoromethyl)phenyl]piperidin-4-yl]methyl](pyrid-4-ylmethyl) amine;

N-methyl-1-[1-[(4-phenylpiperazin-1-yl)acetyl]-4-[3-(trifluoromethyl)phenyl]piperidin-4-yl]methaneamine;

N,N-dimethyl-1-[1-[(4-phenylpiperazin-1-yl)acetyl]-4-[3-(trifluoromethyl)phenyl]piperidin-4-yl]methaneamine N-methyl-N-[[1-[(4-phenylpiperazin-1-yl)acetyl]-4-[3-(trifluoromethyl)phenyl]piperidin-4-yl]methyl]-ethaneamine;

[[1-[[4-(4-fluorophenyl)piperazin-1-yl]acetyl]-4-[3-(trifluoromethyl)phenyl]piperidin-4-yl]methyl]-amine;

[[1-[[4-(3-methoxyphenyl)piperazin-1-yl]acetyl]-4-[3-(trifluoromethyl)phenyl]piperidin-4-yl]methyl]-amine;

[[1-[[4-(3,4-dichlorophenyl)piperazin-1-yl]-acetyl]-4-[3-(trifluoromethyl)phenyl]piperidin-4-yl]methyl]amine;

[[1-[[4-(2,4-dimethylphenyl)piperazin-1-yl]-acetyl]-4-[3-(trifluoromethyl)phenyl]piperidin-4-yl]methyl]methylamine;

[[1-[[4-(2,4-dimethylphenyl)piperazin-1-yl]-acetyl]-4-[3-(trifluoromethyl)phenyl]piperidin-4-yl]methyl]dimethylamine;

[[1-[[4-(3,4-dimethoxyphenyl)piperazin-1-yl]-acetyl]-4-[3-(trifluoromethyl)phenyl]piperidin-4-yl]methyl] amine;

[[1-[[4-(3,4-dimethoxyphenyl)piperazin-1-yl]-acetyl]-4-[3-(trifluoromethyl)phenyl]piperidin-4-yl]methyl]dimethylamine;

N-ethyl-N-[[1-[[4-(3-methoxyphenyl)piperazin-1-yl] acetyl]-4-[3-(trifluoromethyl)phenyl]piperidin-4-yl] methyl]ethaneamine;

1-[2-[4-(azetidin-1-ylcarbonyl)-4-[3-(trifluoromethyl) phenyl]piperidin-1-yl]-2-oxoethyl]-4-phenylpiperazine;

[[1-[[4-(3,4-dimethoxyphenyl)piperazin-1-yl]-acetyl]-4-[3-(trifluoromethyl)phenyl]piperidin-4-yl]methyl]methylamine;

1-[[4-(4-chlorophenyl)piperazin-1-yl]acetyl]-4-[3-(trifluoromethyl)phenyl]piperidin-4-ol;

1-[[4-(3-chlorophenyl)piperazin-1-yl]acetyl]-4-[3-(trifluoromethyl)phenyl]piperidin-4-ol;

1-[[4-(4-methoxyphenyl)piperazin-1-yl]acetyl]-4-[3-(trifluoromethyl)phenyl]piperidin-4-ol;

1-[[4-(3-methoxyphenyl)piperazin-1-yl]acetyl]-4-[3-(trifluoromethyl)phenyl]piperidin-4-ol;

1-[(4-phenylpiperazin-1-yl)acetyl]-4-[3-(trifluoromethyl) phenyl]piperidine-4-carboxamide;

1-[[4-(2,4-dimethylphenyl)piperazin-1-yl]acetyl]-4-[3-(trifluoromethyl)phenyl]piperidine-4-carboxamide;

1-[[4-(2,4-dimethoxyphenyl)piperazin-1-yl]acetyl]-4-[3-(trifluoromethyl)phenyl]piperidine-4-carboxamide;

1-[[4-(2,4-dichlorophenyl)piperazin-1-yl]acetyl]-4-[3-(trifluoromethyl)phenyl]piperidine-4-carboxamide;

1-3-(4-phenylpiperazin-1-yl)propanoyl]-4-[3-(trifluoromethyl)phenyl]piperidin-4-ol;

1-[3-[4-(4-methylphenyl)piperazin-1-yl]propanoyl]-4-[3-(trifluoromethyl)phenyl]piperidin-4-ol;

1-[3-[4-(4-fluorophenyl)piperazin-1-yl]propanoyl]-4-[3-(trifluoromethyl)phenyl]piperidin-4-ol;

1-[3-[4-(4-methoxyphenyl)piperazin-1-yl]propanoyl]-4-[3-(trifluoromethyl)phenyl]-piperidin-4-ol;

[[1-[[4-(3,4-dimethoxyphenyl)piperazin-1-yl]-acetyl]-4-[3-(trifluoromethyl)phenyl]piperidin-4-yl]methyl](2-furylmethyl)methylamine;

(3-furylmethyl)[[1-[(4-phenylpiperazin-1-yl)acetyl]-4-[3-(trifluoromethyl)phenyl]piperidin-4-yl]methyl]amine;

[[1-[[4-(2,3-dimethylphenyl)piperazin-1-yl]-acetyl]-4-[3-(trifluoromethyl)phenyl]piperidin-4-yl]methyl]amine;

in the form of base or an addition salt of an acid, and in the form of a hydrate or solvate.

In the text below a protective group Pg is a group which on the one hand allows a reactive function such as a hydroxyl or an amine to be protected during a synthesis and on the other hand allows the reactive function to be regenerated intact at the end of synthesis. Examples of protective groups and also of methods of protection and deprotection are given in "Protective Groups in Organic Synthesis", Green et al., 2nd edition (John Wiley & sons, Inc., New York).

A leaving group in the text below is a group which can be easily cleaved from a molecule by breaking a heterolytic bond, with departure of an electron pair. This group may therefore be replaced easily by another group in the course of a substitution reaction, for example. Such leaving groups are, for example, halogens or an activated hydroxyl group such as a mesyl, tosyl, triflate, acetyl, etc. Examples of leaving groups and also of references for their preparation are given in "Advances in Organic Chemistry", J. March, 3rd edition, Wiley Interscience, pp. 310-316.

In accordance with the invention, the compounds of formula (I) in which n=1 may be prepared according to a process characterized in that:

a1) a compound of the formula

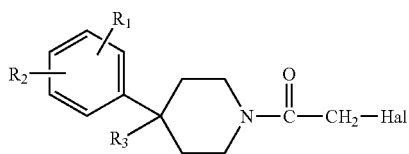
(IIa)

in which $R_1$, $R_2$ and $R_3$ are as defined for a compound of formula (I) and Hal represents a halogen atom, preferably chlorine or bromine, with the proviso that when $R_3$ contains a hydroxyl or amine function these functions can be protected, is reacted with a compound of formula

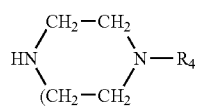
(III)

in which $R_4$ is as defined for a compound of formula (I);

b1) and, following deprotection where appropriate of the hydroxyl or amine functions present in $R_3$, the compound of formula (I) is obtained.

Where appropriate, the compound of formula (I) is converted into one of its addition salts with an acid.

In accordance with the invention, the compounds of formula (I) in which n=2, may be prepared according to a process characterized in that:

a2) a compound of formula

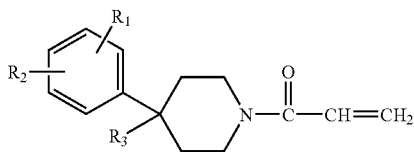
(IIb)

in which $R_1$, $R_2$ and $R_3$ are as defined for a compound of formula (I), with the proviso that when $R_3$ contains a hydroxyl or amine function these functions can be protected, is reacted with a compound of formula

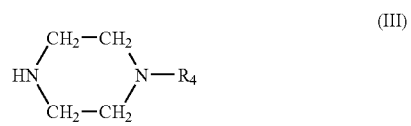
(III)

in which $R_4$ is as defined for a compound of formula (I);

b2) and, following deprotection where appropriate of the hydroxyl or amine functions present in $R_3$, the compound of formula (I) is obtained.

Where appropriate, the compound of formula (I) is converted into one of its addition salts with an acid.

In step a1) or in step a2), when a compound of formula (IIa) or (IIb) is reacted with a compound of formula (III), the reaction is carried out in the presence of a base selected from organic bases such as triethylamine, N,N-diisopropylethylamine or N-methylmorpholine or from alkali metal carbonates or bicarbonates such as potassium carbonate, sodium carbonate or sodium bicarbonate and in the absence or presence of an alkali metal iodide such as potassium iodide or sodium iodide. The reaction is carried out in a solvent such as acetonitrile, N,N-dimethylformamide, toluene or propan-2-ol and at a temperature between the ambient temperature and the reflux temperature of the solvent.

Where appropriate, in step b1) or in step b2), the hydroxyl or amine functions present in $R_3$ are deprotected in accordance with the conventional methods well known to the person skilled in the art.

In one version of the process and when $R_3$ represents a group —$CH_2NR_{10}R_{11}$ in which $R_{10}$ and $R_{11}$ each represent hydrogen a3) a compound of formula

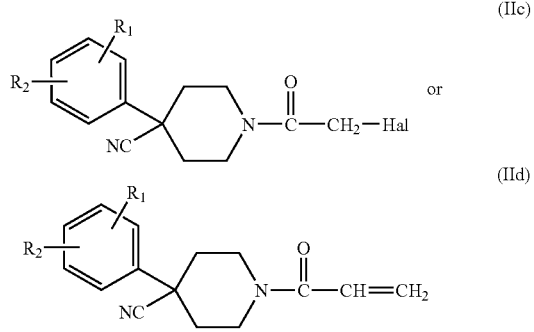
(IIc)
or
(IId)

in which $R_1$ and $R_2$ are as defined for a compound of formula (I) and Hal represents a halogen atom, preferably chlorine or bromine, is reacted with a compound of formula

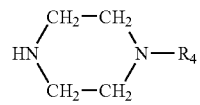
(III)

in which $R_4$ is as defined for a compound of formula (I), to give a compound of formula

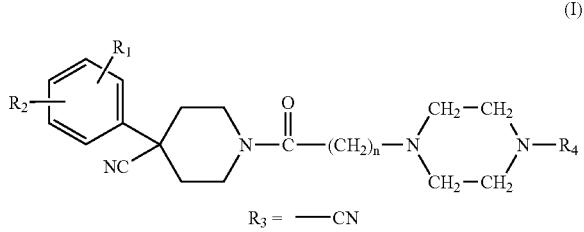

$R_3 = \text{—CN}$ b3) the cyano group of the compound of formula (I) is reduced to give a compound of formula (I) in which $R_3=CH_2NH_2$.

Where appropriate the compound of formula (I) is converted into one of its addition salts with an acid.

In step a3) the reaction between the compound of formula (IIc) or (IId) and the compound of formula (III) is carried out as described above in step a1) or a2) of the process according to the invention.

In step b3) the reduction of the cyano group of the compound of formula (I) in which $R_3$=—CN is carried out in accordance with conventional methods. Thus, for example, the reduction is carried out by hydrogenation in the presence of a catalyst such as Raney® nickel or rhodium on alumina and in the presence or absence of ammonia in a solvent such as methanol, N,N-dimethylformamide or tetrahydrofuran or a mixture of these solvents and at a temperature between ambient temperature and 60° C.

In another version of the process and when $R_3$ represents a group —$CH_2NR_{10}R_{11}$ in which $R_{11}$ represents a group —$CH_2R_{14}$:

a4) a compound of formula:

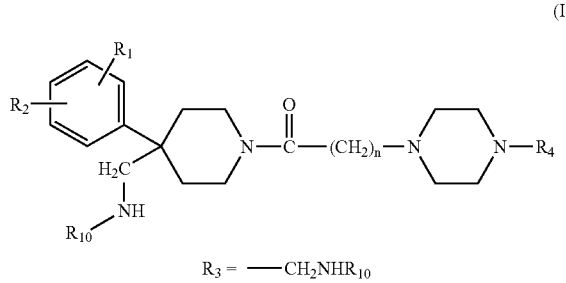

$R_3 = \text{—}CH_2NHR_{10}$ in which $R_1$, $R_2$, $R_4$, $R_{10}$ and n are as defined for a compound of formula (I) is reacted with a compound of formula:

in which $R_{14}$ is as defined for a compound of formula (I), in the presence of an acid, in a solvent, and then the iminium salt intermediately formed is reduced by means of a reducing agent.

Where appropriate the compound of formula (I) is converted into one of its addition salts with an acid.

The reaction takes place in the presence of an acid such as acetic acid, in a solvent such as dichloromethane or tetrahydrofuran, at a temperature between the ambient temperature and the reflux temperature of the solvent, and forms in situ an imine intermediate which is reduced chemically using, for example, sodium cyanoborohydride or sodium triacetoxyborohydride, or catalytically using hydrogen and a catalyst such as palladium on carbon or Raney® nickel.

A compound of formula (I) in which $R_3$ represents a group —$CH_2NR_{10}R_{11}$ in which $R_{10}$=H and $R_{11}$=($C_1$-$C_4$)alkyl may also be prepared by reacting a compound of formula (I) in which $R_3$=—$CH_2NH_2$ with a ($C_1$-$C_4$)alkyl halide in the presence of a base such as an alkali metal carbonate such as potassium carbonate in a solvent such as acetonitrile, N,N-dimethylformamide or tetrahydrofuran at a temperature between the ambient temperature and the reflux temperature of the solvent. An identical reaction is used to prepare the compounds of formula (I) in which $R_{10}$ and $R_{11}$ each represent the same or a different ($C_1$-$C_4$)alkyl.

A compound of formula (I) in which $R_3$ represents a group —$CH_2NR_{10}R_{11}$ in which $R_{10}$=H or ($C_1$-$C_4$)alkyl and $R_{11}$=($C_1$-$C_4$)alkyl may also be prepared by reacting a compound of formula (I) in which $R_3$=—$CH_2$—$NHR_{10}$ with formaldehyde or with an aldehyde of formula OHC—($C_1$-$C_4$)alkyl, or with a corresponding ketone, in the presence of a reducing agent such as sodium borohydride or sodium triacetoxyborohydride and in the presence of an acid such as acetic acid in a solvent such as dichloromethane or tetrahydrofuran at a temperature between 0° C. and the ambient temperature.

A compound of formula (I) in which $R_3$ represents a group —$CH_2NR_{10}R_{11}$ in which $R_{10}$ and $R_{11}$, together with the nitrogen atom to which they are attached, constitute aziridine may also be prepared by cyclizing a corresponding intermediate in which $R_3$ represents a group —$CH_2NH$—$CH_2CH_2$—Cl in the presence of a base such as an alkali metal carbonate such as potassium carbonate and in the presence of an alkali metal iodide such as potassium iodide in a solvent such as acetonitrile and at a temperature between the ambient temperature and the reflux temperature of the solvent; the corresponding intermediate is prepared by reacting a compound of formula (I) in which $R_3$=—$CH_2NH_2$ with chloroacetaldehyde by the method described above.

A compound of formula (I) in which $R_3$ represents a group —$CH_2NR_{10}R_{11}$ in which $R_{10}$ and $R_{11}$, together with the nitrogen atom to which they are attached, constitute azetidine, pyrrolidine, piperidine or morpholine, respectively, may also be prepared by reacting a compound of formula (I) in which $R_3$=—$CH_2NH_2$ with a compound of formula Hal-($CH_2$)$_3$-Hal, Hal-($CH_2$)$_4$-Hal, Hal-($CH_2$)$_5$-Hal or Hal-$CH_2CH_2$—O—$CH_2CH_2$-Hal respectively, in which Hal represents a halogen atom, preferably chlorine or bromine, in the presence of a base such as an alkali metal carbonate such as potassium carbonate or in the presence of an alkali metal iodide such as potassium iodide in a solvent such as acetonitrile, ethylene glycol or a mixture of these solvents and at a temperature between the ambient temperature and the reflux temperature of the solvent.

A compound of formula (I) in which $R_3$ represents a group —$CONR_{12}R_{13}$ may also be prepared by reacting a corresponding intermediate in which $R_3$ represents a carboxyl with a compound of formula $HNR_{12}R_{13}$ by conventional methods of peptide coupling; the corresponding intermediate is prepared by conventional methods by acid or base treatment of a compound of formula (I) in which $R_3$ represents a ($C_1$-$C_4$) alkoxycarbonyl or by reacting a compound of formula (I) in which $R_3$=—CN with a strong base such as an alkali metal hydroxide such as potassium hydroxide in a solvent such as toluene or ethylene glycol at a temperature between the ambient temperature and the reflux temperature of the solvent.

A compound of formula (I) in which $R_3$ represents a group —$CH_2OR_5$ in which $R_5$ represents a hydrogen atom may also be prepared by acid or base treatment of a corresponding intermediate in which $R_3$ represents a group —$CH_2OCO(C_1$-$C_4)$alkyl.

The compounds of formula (I) thus obtained may be subsequently separated from the reaction medium and purified by conventional methods, for example by crystallization or chromatography.

The compounds of formula (I) thus obtained are isolated in the form of the free base or a salt, by conventional techniques.

The compounds of formula (IIa) are prepared by reacting a piperidine derivative of formula

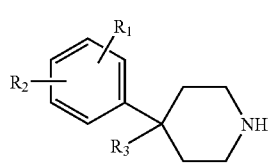

(V)

in which $R_1$, $R_2$ and $R_3$ are as defined for a compound of formula (I) with a compound of formula

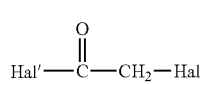

(VI)

in which Hal and Hal' represent each independently a halogen atom, preferably chlorine or bromine. The reaction is carried out in the presence of a base such as triethylamine, N,N-diisopropylethylamine or N-methylmorpholine in a solvent such as dichloromethane, chloroform, tetrahydrofuran, dioxane or a mixture of these solvents and at a temperature between 0° C. and the ambient temperature.

The compounds of formula (IIb) are prepared by reacting the compound of formula (V) with a compound of formula

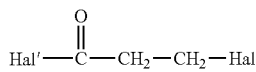

(VII)

in which Hal and Hal' are as defined above under the operating conditions mentioned above.

Similarly the compounds of formula (IIc) or (IId) respectively are prepared by reacting a compound of formula

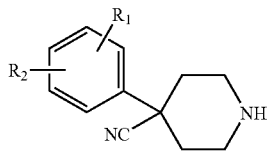

(Va)

in which $R_1$ and $R_2$ are as defined for a compound of formula (I) with a compound of formula (VI) or (VII) respectively in accordance with the same operating conditions as above.

The compounds of formula (VI) or (VII) are available commercially, are known or are prepared by known methods.

The compounds of formula (III) are available commercially or are prepared by known methods such as those described in Tetrahedron Lett., 1996, 37 (47), 8487-8488; Tetrahedron Lett., 1997, 38 (39), 6875-6876; Tetrahedron Lett., 2000, 41 (16), 2881-2884; Syn. Lett., 2000, 5, 674-676; Bioorg. Med. Chem. Lett., 2000, 10, 2489-2491; Bioorg. Med. Chem., 2002, 10, 4023-4027.

The compounds of formula (IV) are available commercially or are described in the literature, or else may be prepared according to methods which are described therein, such as in J. Org. Chem., 1961, 26, 2976; Chim. Ind. (Milan), 1968, 50, 264; J. Med. Chem., 1970, 13, 1208-1212; J. Heterocycl. Chem., 1990, 27 (1), 1-12; Synth. Commun., 1995, 25 (9), 1383-1390; Bioorg. Med. Chem. Lett., 2003, 13 (3), 463-466.

The compounds of formula (V) are available commercially, are known or are prepared by known methods such as those described in EP-0 474 561, EP-0 673 928 or WO 96/23787.

The compounds of formula (V) are generally prepared in a form in which they are protected on the nitrogen atom of the piperidine; after a step of deprotection the compounds of formula (V) themselves are obtained.

In particular a compound of formula (V) in which $R_3$ represents a group —$OR_5$ in which $R_5$=H is prepared by reacting an organomagnesium derivative of formula

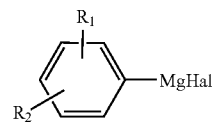

(VIII)

in which $R_1$ and $R_2$ are as defined for a compound of formula (I) and Hal represents a halogen atom, preferably bromine, with 1-benzyl-4-piperidinone in a solvent such as diethyl ether or tetrahydrofuran at a temperature between the ambient temperature and reflux temperature of the solvent.

The organomagnesium derivatives of formula (VIII) are prepared by conventional methods well known to the person skilled in the art from the corresponding halogenated derivatives.

From compounds of formula (V) in which $R_3$=—OH the compounds of formula (V) in which $R_3$=—$OR_5$ in which $R_5$ represents a $(C_1$-$C_4)$alkyl are prepared by an alkylation reaction by methods which are known to the person skilled in the art.

The compounds of formula (V) in which $R_3$=—OH and which carry a protective group on the nitrogen atom of the piperidine may undergo a Ritter reaction by the action of acetonitrile in an acidic medium in order to prepare the compounds of formula (V) in which $R_3$=—$NHCOCH_3$ by the method described in EP-0 474 561. Hydrolysis in a strong acidic medium is then used to prepare the compounds of formula (V) in which $R_3$=—$NR_6R_7$ in which $R_6$=$R_7$=H. The methods described in EP-0 673 928 or WO 96/23787 are used to prepare the compounds of formula (V) in which $R_3$=—$NR_6R_7$ in which $R_6$ and/or $R_7$ represents a $(C_1$-$C_4)$alkyl.

The compounds of formula (V) in which $R_3$=—$NR_8COR_9$ in which $R_9$ is a $(C_1$-$C_4)$alkyl or else $R_3$=—$CH_2NR_{10}R_{11}$ in which $R_{10}$ and $R_{11}$ represent each independently a hydrogen or a $(C_1$-$C_4)$alkyl or else $R_3$=$(C_1$-$C_4)$alkoxycarbonyl, or else $R_3$=—$CONR_{12}R_{13}$ are prepared by the methods described in WO 96/23787.

A compound of formula (V) in which $R_3$=—$CH_2NR_{10}R_{11}$ in which $R_{10}$=$R_{11}$=H is prepared from the compound of formula (Va) by the method described above for a compound of formula (I).

A compound of formula (V) in which $R_3$=—$CH_2NR_{10}R_{11}$ in which $R_{10}$=H or $(C_1$-$C_4)$alkyl and $R_{11}$=$(C_1$-$C_4)$alkyl or a group —$CH_2R_{14}$ is prepared by the method described above for a compound of formula (I).

A compound of formula (V) in which $R_3$=—$CH_2NR_{10}R_{11}$ in which $R_{10}$=H and $R_{11}$=—$CH_3$ may also be prepared by reducing a corresponding intermediate in which $R_3$=—$CH_2NHCHO$ using a reducing agent such as lithium aluminium hydride in a solvent such as ether or tetrahydrofuran at a temperature between the ambient temperature and the reflux temperature of the solvent. The corresponding intermediate is prepared by reacting a compound of formula (V) in which $R_3$=—$CH_2NH_2$ with ethyl formate at a temperature between the ambient temperature and 60° C.

A compound of formula (V) in which $R_3$=—$CH_2NR_{10}R_{11}$ in which $R_{10}$ and $R_{11}$, together with the nitrogen atom to which they are attached, constitute aziridine, azetidine, pyrrolidine, piperidine or morpholine is prepared by the methods described above for a compound of formula (I).

A compound of formula (V) in which $R_3$=—$CONR_{12}R_{13}$ in which $R_{12}$=$R_{13}$=H may also be prepared by reacting a compound of formula (Va), protected on the nitrogen atom of the piperidine, with hydrogen peroxide in the presence of a strong base such as an alkali metal hydroxide such as sodium hydroxide and a phase transfer catalyst such as a substituted quaternary ammonium salt, triethylammonium chloride for example, in a solvent such as toluene in a mixture with water, at a temperature between the ambient temperature and the reflux temperature of the solvent.

The compounds of formula (Va) are prepared by known methods such as those described in Bioorg. Med. Chem. Lett., 1999, 9, 3273-3276 and in J. Med. Chem., 1999, 42 (23), 4778-4793.

From compounds of formula (V) in which $R_3$=—$CH_2OH$ the compounds of formula (V) in which $R_3$=—$CH_2OR_5$ in which $R_5$ represents a $(C_1$-$C_4)$alkyl are prepared by an alkylation reaction by the methods known to the person skilled in the art.

The compounds of formula (V) in which $R_3$=—$CH_2OR_5$ in which $R_5$ represents a hydrogen atom are prepared by reducing a compound of formula (V) in which $R_3$ represents a methoxycarbonyl by methods known to the person skilled in the art.

The compounds of formula (V) in which $R_3$ represents a $(C_1$-$C_4)$alkoxycarbonyl are prepared by esterification reaction of a corresponding intermediate in which $R_3$ represents a carboxyl by methods known to the person skilled in the art; the corresponding intermediate is prepared by reacting a compound of formula (Va) with a strong base such as an alkali metal hydroxide such as potassium hydroxide, in a solvent such as toluene or ethylene glycol at a temperature between the ambient temperature and the reflux temperature of the solvent.

The N-protective groups used where appropriate are conventional N-protective groups which are well known to the person skilled in the art, such as, for example, the tert-butoxycarbonyl, fluorenylmethoxycarbonyl, benzyl, benzhydrylidene or benzyloxycarbonyl group.

The following examples describe the preparation of certain compounds in accordance with the invention. These examples are not limitative and merely illustrate the present invention. The numbers of the compounds exemplified refer to those given in Table I below, which illustrates the chemical structures and the physical properties of some compounds according to the invention.

EXAMPLES

In the preparations and in the examples the following abbreviations are used:
ether: diethyl ether
iso ether: diisopropyl ether
DMSO: dimethyl sulphoxide
DMF: N,N-dimethylformamide
THF: tetrahydrofuran
DCM: dichloromethane
AcOEt: ethyl acetate
DIPEA: diisopropylethylamine
TFA: trifluoroacetic acid
BOP: benzotriazol-1-yloxytris(dimethylamino)phosphonium hexafluorophosphate
PyBOP: benzotriazol-1-yloxytripyrrolidinophosphonium hexafluorophosphate
2N hydrochloric ether: 2N solution of hydrochloric acid in diethyl ether
m.p.: melting point
AT: ambient temperature
b.p.: boiling temperature
HPLC: high performance liquid chromatography
Silica H: Silica gel 60H sold by Merck (Darmstadt)
Buffer solution pH=2: solution of 16.66 g of $KHSO_4$ and 32.32 g of $K_2SO_4$ in one litre of water.

The proton magnetic resonance ($^1H$ NMR) spectra are recorded at 200 MHz in DMSO-$d_6$, using the DMSO-$d_6$ peak as reference. The chemical shifts δ are expressed in parts per million (ppm). The signals observed are expressed as follows: s: singlet; bs: broad singlet; d: doublet; sd: split doublet; t: triplet; st: split triplet; q; quadruplet; unres. comp.: unresolved complex; mt: multiplet.

The NMR spectra confirm the structures of the compounds.

The compounds according to the invention are analysed by LC/UV/MS (liquid chromatography/UV detection/mass spectrometry) coupling.

For the compounds a check is made that their mass spectra as obtained in the positive electrospray mode (ESI+) are compatible with the calculated molar mass.

The mass spectra of the compounds according to the invention generally have as their base peak the molecular ion MH+.

Preparations

1. Preparations of Compounds of Formulae (V) and (Va)

Preparation 1.1

4-[3-(Trifluoromethyl)phenyl]-4-piperidinol hydrochloride (V), HCl: $R_1$=3-$CF_3$; $R_2$=H; $R_3$=—OH.

A) 1-Benzyl-4-[3-(trifluoromethyl)phenyl]-4-piperidinol hydrochloride

A mixture of 180 g of magnesium in 2670 ml of THF is heated to 30° C. and admixed with 33 ml of a solution of 1670 g of 1-bromo-3-(trifluoromethyl)benzene in 1330 ml of THF and then, slowly, with the remainder of the solution so as to bring about and subsequently maintain reflux of the THF, and is left at reflux with stirring for 2 hours. Subsequently a solution of 1000 g of 1-benzyl-4-piperidinone in 3200 ml of THF is added slowly and the mixture is heated at reflux for 2 hours.

After cooling to AT, the reaction mixture is introduced over 30 minutes into a solution of 1870 g of ammonium chloride in 6700 ml of water and the mixture is left with stirring at 20-25° C. for 2 hours. After decanting, the organic phase is washed with 5330 ml of water and the solvent is evaporated under vacuum. The residue is taken up in 5330 ml of ether, a solution of 210 g of HCl gas in 800 ml of propan-2-ol is added slowly, the temperature being kept below 25° C., the mixture is left with stirring for 40 minutes and the crystals formed are isolated with suction. The crystals are taken up in 2000 ml of ether and again isolated with suction. 1080 g of the expected product are obtained following recrystallization from a propan-2-ol/EtOH (70/30; v/v) mixture.

B) 4-[3-(Trifluoromethyl)phenyl]-4-piperidinol hydrochloride

A mixture of 1000 g of the compound obtained in the preceding step and 83 g of 10% palladium on carbon (50% moisture content) in 2910 ml of EtOH and 2910 ml of MeOH is hydrogenated at 50° C. under a pressure of 2 bars. The catalyst is filtered off and washed twice with 660 ml of MeOH and the filtrate and washings are concentrated under vacuum. The residue is taken up in 3320 ml of ether and is left with stirring at AT for 1 hour 30 minutes. The precipitate formed is isolated with suction, washed with 280 ml of ether and dried under vacuum at 40° C. This gives 726 g of the expected product.

Preparation 1.2

4-[3-(Trifluoromethyl)phenyl]-4-piperidinecarbonitrile hydrochloride (Va), HCl: $R_1$=3-$CF_3$; $R_2$=H.

A) 2-(2,2-Diethoxyethyl)-4,4-diethoxy-2-[3-(trifluoromethyl)phenyl]butanenitrile A mixture of 30 g of 3-trifluoromethyl)phenylacetonitrile and 14.4 g of sodium amide in 400 ml of toluene is left with stirring at AT for 5 minutes, 66 ml of bromoacetaldehyde diethyl acetal are added and the mixture is then heated at 60° C. for 3 hours. It is concentrated under vacuum, the residue is taken up in water and extracted with ether, the organic phase is dried over $Na_2SO_4$ and the solvent is evaporated under vacuum. The residue is chromatographed on silica gel H, eluting with a DCM/AcOEt (100/5; v/v) mixture. This gives 26 g of the expected product.

B) 4-Oxo-2-(2-oxoethyl)-2-[3-(trifluoromethyl)phenyl]butanenitrile

A mixture of 23.9 g of the compound obtained in the preceding step in 90 ml of formic acid is left with stirring at 50° C. for 1 hour. Water is added to the reaction mixture, which is then extracted with AcOEt, the organic phase is washed with water and with 10% $NaHCO_3$ solution and dried over $Na_2SO_4$ and the solvent is evaporated under vacuum. This gives 16 g of the expected product, which is used immediately in the following step.

C) 1-Benzyl-4-[3-(trifluoromethyl)phenyl]-4-piperidinecarbonitrile hydrochloride A mixture of 16 g of the compound obtained in the preceding step, 6.25 ml of benzylamine, 48.6 g of sodium triacetoxyborohydride and 5 drops of acetic acid in 150 ml of DCM is left with stirring at AT overnight. Subsequently 40 ml of MeOH are added dropwise and the mixture is then heated at 60° C. for 1 hour. The reaction mixture is concentrated under vacuum, the residue is extracted with AcOEt, the organic phase is washed with 10% $NaHCO_3$ solution and with water and dried over $Na_2SO_4$ and the solvent is evaporated under vacuum. The residue is taken up in a saturated solution of HCl gas in ether and the precipitate formed is isolated with suction. This gives 18 g of the expected product.

D) 4-[3-(Trifluoromethyl)phenyl]-4-piperidinecarbonitrile hydrochloride

A mixture of 2 g of the compound obtained in the preceding step and 0.2 g of 10% palladium on carbon in 30 ml of MeOH is hydrogenated at AT at atmospheric pressure for 3 hours. The catalyst is filtered off on Celite® and the filtrate is concentrated under vacuum. This gives 1.5 g of the expected product.

This compound can also be prepared by following the three steps below:

A') tert-Butyl bis(2-chloroethyl)carbamate

A mixture of 106 g of N,N-bis(2-chloroethyl)amine hydrochloride and 130 g of di-tert-butyl dicarbonate in 1500 ml of DCM is admixed dropwise over 1 hour 30 minutes at AT with 83 ml of triethylamine, then left with stirring at AT overnight. The reaction mixture is washed with water and the organic phase is dried over $Na_2SO_4$ and evaporated under vacuum. This gives 150 g of the expected product, which is used as it is.

B') tert-Butyl 4-cyano-4-[3-(trifluoromethyl)phenyl]-1-piperidine carboxylate

A suspension of 56 g of sodium hydride at a concentration of 60% in oil in 750 ml of DMSO in 250 ml of THF is admixed dropwise under an inert atmosphere and at AT with a solution of 120 g of 3-(trifluoromethyl)phenylacetonitrile in 250 ml of DMSO and then, slowly with a solution of 150 g of the compound obtained in the preceding step in 250 ml of DMSO and heated at 60° C. overnight. The reaction mixture is poured into an ice/$H_2O$ mixture and extracted with ether, the organic phase is washed with water and with saturated NaCl solution and dried over $Na_2SO_4$ and the solvent is evaporated under vacuum. The residue is chromatographed on silica gel, eluting with DCM and then with a DCM/AcOEt (80/20; v/v) mixture. This gives 191 g of the expected product, which crystallizes; m.p.=72-73° C.

C') 4-[3-(Trifluoromethyl)phenyl]-4-piperidinecarbonitrile hydrochloride

A mixture of 115 g of the compound obtained in the preceding step, 500 ml of a 2N solution of HCl in ether and 150 ml of MeOH is left with stirring at AT for 4 hours. The crystalline product formed is isolated with suction and dried. This gives 75 g of the expected product, m.p.=259° C.

Preparation 1.3 tert-Butyl[4-[3-(trifluoromethyl)phenyl]-4-piperidyl]methylcarbamate (V): $R_1$=3-$CF_3$; $R_2$=H; $R_3$=—$CH_2$NH—COOC$(CH_3)_3$.

A) [1-Benzyl-4-[3-(trifluoromethyl)phenyl]-4-piperidyl]methylamine

A mixture of 1.5 g of the compound obtained in step C of preparation 1.2, 0.15 g of Raney® nickel and 5 ml of aqueous ammonia in 20 ml of MeOH is hydrogenated at AT under atmospheric pressure overnight. The catalyst is filtered off and the filtrate is concentrated under vacuum. This gives 1.45 g of the expected product.

B) tert-Butyl[1-benzyl-4-[3-(trifluoromethyl)phenyl]-4-piperidyl]methylcarbamate A mixture of 1.45 g of the compound obtained in the preceding step and 20 ml of AcOEt is heated to 40° C., 0.9 g of di-tert-butyl dicarbonate is added and the mixture is then heated at reflux for 30 minutes. After cooling to AT it is admixed with water and extracted with AcOEt, the organic phase is dried over $Na_2SO_4$ and the solvent is evaporated under vacuum. This gives 1.86 g of the expected product.

C) tert-Butyl[4-[3-(trifluoromethyl)phenyl]-4-piperidyl]methylcarbamate

A mixture of 1.8 g of the compound obtained in the preceding step and 0.18 g of 10% palladium on carbon in 20 ml of MeOH is hydrogenated at AT at atmospheric pressure overnight. The catalyst is filtered off and the filtrate is concentrated under vacuum. This gives 1.3 g of the expected product in the form of an oil.

Preparation 1.4 tert-Butylmethyl[[4-[3-(trifluoromethyl)phenyl]piperidin-4-yl]methyl]carbamate (V): $R_1$=3-$CF_3$; $R_2$=H; $R_3$=—$CH_2$N($CH_3$)—COOC$(CH_3)_3$

A) N,N-Bis(2-chloroethyl)benzylamine

An ice bath is used to cool a mixture of 150 g of N,N-bis(2-chloroethyl)amine hydrochloride and 100 ml of benzyl bromide in 1000 ml of DMF and then 120 ml of triethylamine are added dropwise and the mixture is left with stirring at AT overnight. The reaction mixture is concentrated under vacuum, the residue is taken up in water and extracted 3 times with ether, the organic phases are dried over $Na_2SO_4$ and the solvent is evaporated under vacuum. This gives 113 g of the expected product.

B) 1-Benzyl-4-[3-(trifluoromethyl)phenyl]-4-piperidinecarbonitrile hydrochloride A suspension of 23.24 g of sodium hydride at a concentration of 60% in oil in 100 ml of DMSO and 100 ml of THF is admixed dropwise under an inert atmosphere and at AT with a solution of 50 g of 3-(trifluoromethyl)phenylacetonitrile in 150 ml of DMSO and the mixture is left with stirring for 15 minutes. A solution of 62.43 g of the compound obtained in the preceding step in 150 ml of DMSO is subsequently added over 1 hour and the mixture is left with stirring at AT overnight. An ice/water mixture is added, the system is extracted with ether, the organic phase is dried over $Na_2SO_4$ and the solvent is evaporated under vacuum. The residue is taken up in 1000 ml of hot EtOH, the system is left with stirring at AT for 48 hours and the crystalline product formed is isolated with suction. This gives 50 g of the expected product.

C) [1-Benzyl-4-[3-(trifluoromethyl)phenyl]-4-piperidyl]methylamine 30 g of the compound obtained in the preceding step are dissolved in 10% NaOH solution and extracted with ether, the organic phase is dried over $Na_2SO_4$ and the solvent is evaporated under vacuum. The product, in the form of the free base, is taken up in 500 ml of MeOH and 30 ml of 20% aqueous ammonia solution, 3 g of Raney® nickel are added and the system is hydrogenated at AT under atmospheric pressure overnight. The catalyst is filtered off and the filtrate is concentrated under vacuum. The residue is taken up in water and extracted with AcOEt, the organic phase is dried over $Na_2SO_4$ and the solvent is evaporated under vacuum. This gives 27 g of the expected product.

D) [[1-Benzyl-4-[3-(trifluoromethyl)phenyl]-4-piperidyl]methyl]formamide

A mixture of 27 g of the compound obtained in the preceding step and 300 ml of ethyl formate is left with stirring at AT overnight, then heated at 60° C. for 6 hours and left with stirring at AT for 48 hours. It is concentrated under vacuum, the residue is taken up with 10% HCl solution, the acidic aqueous phase is washed with ether, ice is added and the mixture is rendered alkaline by addition of 10% NaOH solution and extracted with ether, the organic phase is dried over $Na_2SO_4$ and the solvent is evaporated under vacuum. The residue is chromatographed on silica gel H, eluting with DCM and then with a DCM/MeOH (100/4; v/v) mixture. This gives 20 g of the expected product.

E) [[1-Benzyl-4-[3-(trifluoromethyl)phenyl]-4-piperidyl]methyl]methylamine

A suspension of 4 g of lithium aluminium hydride in 400 ml of ether is admixed at AT with 20 g of the compound obtained in the preceding step and then left with stirring at AT for 16 hours. Subsequently, in succession, 3 ml of water, 3 ml of 30% NaOH and 1 ml of water are added and the mixture is left with stirring. The mineral salts are filtered off on Celite, the filtrate is decanted, the organic phase is dried over $Na_2SO_4$ and the solvent is evaporated under vacuum. This gives 18 g of the expected product.

F) tert-Butyl[[1-benzyl-4-[3-(trifluoromethyl)phenyl]-4-piperidyl]methyl]methylcarbamate A mixture of 18 g of the compound obtained in the preceding step and 9.6 g of di-tert-butyl dicarbonate in 300 ml of DCM is left with stirring at AT for 1 hour. Water is added to the reaction mixture, which is then extracted with DCM, the organic phase is dried over $Na_2SO_4$ and the solvent is evaporated under vacuum. The residue is chromatographed on silica gel H, eluting with a DCM/MeOH (100/2; v/v) mixture. This gives 21 g of the expected product.

G) tert-Butylmethyl[4-[3-(trifluoromethyl)phenyl]-piperid-4-yl]methyl]carbamate

A mixture of 21 g of the compound obtained in the preceding step in 2 g of 10% palladium on carbon in 300 ml of MeOH is hydrogenated at AT under atmospheric pressure for 12 hours. The catalyst is filtered off and the filtrate is concentrated under vacuum. This gives 16 g of the expected product.

Preparation 1.5

N,N-Dimethyl-1-[4-[3-(trifluoromethyl)phenyl]piperidin-4-yl]methanamine dihydrochloride (V), 2HCl: $R_1$=3-$CF_3$; $R_2$=H; $R_3$=—$CH_2N(CH_3)_2$.

A) tert-Butyl 4-(aminomethyl)-4-[3-(trifluoromethyl)phenyl]piperidine-1-carboxylate A mixture of 18.2 g of the compound obtained in step B' of preparation 1.2, 1.8 g of Raney® nickel and 30 ml of ammonia in 600 ml of MeOH is hydrogenated for 2 days at 25° C. and under atmospheric pressure. The catalyst is filtered off and the filtrate is concentrated under vacuum. This gives 18 g of the expected product, which is used as it is.

B) tert-Butyl 4-[(dimethylamino)methyl]-4-[3-(trifluoromethyl)phenyl]piperidine-1-carboxylate A mixture of 18 g of the compound obtained in the preceding step, 9.4 ml of 37% aqueous formaldehyde solution, 1 ml of acetic acid in 500 ml of THF is admixed at AT with 106 g of sodium triacetoxyborohydride and left with stirring at AT overnight. 100 ml of MeOH are added and the mixture is heated at 70° C. for 1 hour 30 minutes. The mixture is concentrated under vacuum, the residue is taken up in water, rendered alkaline by addition of concentrated NaOH and extracted with DCM, the organic phase is washed with water and dried over $Na_2SO_4$ and the solvent is evaporated under vacuum. The residue is chromatographed on silica gel, eluting with a DCM/MeOH (96/4; v/v) mixture. This gives 15.4 g of the expected product in the form of oil, which solidifies.

C) N,N-Dimethyl-1-[4-[3-(trifluoromethyl)phenyl]-piperidin-4-yl]methanamine dihydrochloride A mixture of 15.4 g of the compound obtained in the preceding step, 150 ml of 2N hydrochloric ether solution and 0.5 ml of concentrated HCl in 20 ml of MeOH is left with stirring at AT for 3 hours. The mixture is concentrated under vacuum, the residue is taken up in ether and triturated and the precipitate formed is filtered off with suction. This gives 11.9 g of the expected product, m.p.=240-245° C.

Preparation 1.6

(V), HCl: $R_1$=3-$CF_3$; $R_2$=H; $R_3$=—$COOCH_3$.

A) 1-Benzyl-4-[3-(trifluoromethyl)phenyl]-4-piperidinecarboxylic acid

A mixture of 5 g of the compound obtained in step C of preparation 1.2 and 4.25 g of KOH pellets in 80 ml of ethylene glycol is heated at reflux for 3 hours. After the mixture is cooled to AT, 100 ml of water are added, the mixture is acidified to a pH of 6.5 by adding 10% HCl solution and the precipitate formed is filtered off with suction and dried under vacuum. This gives 3.9 g of the expected product, m.p.=243° C.

B) Methyl 1-benzyl-4-[3-(trifluoromethyl)phenyl]-4-piperidinecarboxylate hydrochloride A mixture of 3 g of the compound obtained in the preceding step and 50 ml of thionyl chloride in 100 ml of DCM is heated at 60° C. for 3 hours. The mixture is concentrated under vacuum and the residue is taken up in 100 ml of MeOH and heated at 60° C. overnight. The mixture is concentrated under vacuum to give 4 g of the expected product, m.p.=230° C.

C) Methyl 4-[3-(trifluoromethyl)phenyl]-4-piperidine-carboxylate hydrochloride

A mixture of 4 g of the compound obtained in the preceding step and 0.4 g of 10% palladium on carbon in 200 ml of MeOH is hydrogenated overnight at AT under atmospheric pressure. The catalyst is filtered off and the filtrate is concentrated under vacuum. This gives 2.5 g of the expected product.

Preparation 1.7

4-(Azetidin-1-ylcarbonyl)-4-[3-(trifluoromethyl)phenyl]piperidine

$R_1$ = 3-$CF_3$; $R_2$ = H; $R_3$ = —CO—N⟨ ⟩.    (V)

A) 4-(Chloroformyl)-4-[3-(trifluoromethyl)phenyl]-piperidine hydrochloride

A mixture of 1 g of the compound obtained in step A of preparation 1.6 and 10 ml of thionyl chloride in 10 ml of DCM is heated at 60° C. for 2 hours. It is concentrated under vacuum to give 1.05 g of the expected product, which is used as it is.

B) 4-(Azetidin-1-ylcarbonyl)-1-benzyl-4-[3-(trifluoromethyl)phenyl]piperidine

A mixture of 1.05 g of the compound obtained in the preceding step, 0.283 g of azetidine and 1.15 ml of triethylamine in 10 ml of DCM is left with stirring at AT overnight. Saturated $K_2CO_3$ solution is added to the reaction mixture, which is then extracted with DCM, the extract is dried over $Na_2SO_4$ and the solvent is evaporated under vacuum. The residue is chromatographed on silica gel, eluting with a DCM/MeOH (97/3; v/v) mixture. This gives 0.43 g of the expected product.

C) 4-(Azetidin-1-ylcarbonyl)-4-[3-(trifluoromethyl)phenyl]piperidine

A mixture of 0.43 g of the compound obtained in the preceding step, 1 g of 10% palladium on carbon and 20 ml of MeOH is hydrogenated at 25° C. under atmospheric pressure overnight. The catalyst is filtered off and the filtrate is concentrated under vacuum. This gives 0.33 g of the expected product, which is used as it is.

Preparation 1.8

4-[3-(Trifluoromethyl)phenyl]-4-piperidinecarboxamide (V): $R_1$=3-$CF_3$; $R_2$=H; $R_3$=—$CONH_2$.

A) 1-Benzyl-4-[3-(trifluoromethyl)phenyl]-4-piperidinecarboxamide

A mixture of 5 g of the compound obtained in step C of preparation 1.2, 30 ml of toluene, 30 ml of 30% $H_2O_2$ solution, 30 ml of 30% NaOH solution and 0.5 g of aliquot 336 (trioctylmethylammonium chloride) is heated at 100° C. for 48 hours. It is concentrated under vacuum, the residue is taken up in water and extracted with DCM, the organic phase is dried over $Na_2SO_4$ and the solvent is evaporated under vacuum. The residue is chromatographed on silica gel H, eluting with a DCM/MeOH (100/3; v/v) mixture. This gives 2.5 g of the expected product.

B) 4-[3-(Trifluoromethyl)phenyl]-4-piperidinecarboxamide

A mixture of 2.5 g of the compound obtained in the preceding step and 0.25 g of 10% palladium on carbon in 30 ml of MeOH is hydrogenated at AT under atmospheric pressure for 48 hours. The catalyst is filtered off and the filtrate is concentrated under vacuum. This gives 1.7 g of the expected product.

2. Preparations of Compounds of Formula (II)

Preparation 2.1

2-Chloro-1-[4-hydroxy-4-[3-(trifluoromethyl)phenyl]-1-piperidyl]-1-ethanone (IIa): $R_1$=3-$CF_3$; $R_2$=H; $R_3$=—OH; Hal=Cl.

A mixture of 5 g of the compound obtained in preparation 1.1 and 10 ml of DIPEA in 40 ml of DCM is admixed dropwise and at AT with 1.63 ml of 2-chloroacetyl chloride and left with stirring for 30 minutes. The reaction mixture is washed with water, the organic phase is dried over $Na_2SO_4$ and the solvent is evaporated under vacuum. The residue is chromatographed on silica gel, eluting with a DCM/MeOH (97/3; v/v) mixture. This gives 5.5 g of the expected product, which is used as it is.

Preparation 2.2 tert-Butyl[1-(2-chloroacetyl)-4-[3-(trifluoromethyl)phenyl]-4-piperidyl]methylcarbamate (IIa): $R_1$=3-$CF_3$; $R_2$=H; $R_3$=—$CH_2NHCOOC(CH_3)_3$,; Hal=Cl.

An ice bath is used to cool a mixture of 4.95 g of the compound obtained in preparation 1.3 and 6.8 ml of triethylamine in 50 ml of DCM which is then admixed dropwise with 1.65 ml of 2-chloroacetyl chloride and left with stirring, during which the temperature is allowed to return to AT. It is concentrated under vacuum, the residue is taken up with saturated $K_2CO_3$ solution and extracted with AcOEt, the organic phase is washed with saturated $K_2CO_3$ solution, with buffer solution pH=2 and with saturated NaCl solution and dried over $Na_2SO_4$ and the mixture is evaporated under vacuum. The residue is chromatographed on silica gel, eluting with DCM/AcOEt (80/20; v/v) mixture. This gives 1.8 g of the expected product, which is used as it is.

Preparation 2.3 tert-Butyl[[1-(2-chloroacetyl)-4-[3-(trifluoromethyl)phenyl]-4-piperidinyl]methyl]methylcarbamate (IIa): $R_1$=3-$CF_3$; $R_2$=H; $R_3$=—$CH_2N(CH_3)COOC(CH_3)_3$; Hal=Cl.

A solution of 14 g of the compound obtained in preparation 1.4 and 5.5 ml of triethylamine in 300 ml of DCM is cooled to −40° C., 3.1 ml of 2-chloroacetyl chloride are added slowly and the mixture is left with stirring, during which the temperature is allowed to return to AT. It is concentrated under vacuum, the residue is taken up in water and extracted with AcOEt, the organic phase is washed with buffer pH=2 and water and dried over $Na_2SO_4$ and the solvent is evaporated under vacuum. This gives 15.33 g of the expected product.

Preparation 2.4

[[1-(2-Chloroacetyl)-4-[3-(trifluoromethyl)phenyl]piperidin-4-yl]methyl]dimethylamine (IIa): $R_1$=3-$CF_3$; $R_2$=H; $R_3$=—$CH_2N(CH_3)_2$; Hal=Cl.

Using an ice bath, a mixture of 0.94 g of the compound obtained in preparation 1.5 in the form of a free base in 20 ml of ether is cooled, 0.66 g of triethylamine is added and then, dropwise over 15 minutes, a solution of 0.27 ml of 2-chloroacetyl chloride in 10 ml of ether is added. The reaction mixture is washed with water, the organic phase is dried over $Na_2SO_4$ and the solution of the expected product in ether is used immediately in the variant of Example 5.

Preparation 2.5

4-(Azetidin-1-ylcarbonyl)-1-(2-chloroacetyl)-4-[3-(trifluoromethyl)phenyl]piperidine (IIa)

$R_1$ = 3-$CF_3$; $R_2$ = H; $R_3$—CO—N⟨ ⟩; Hal = Cl

A mixture of 0.75 g of the compound obtained in preparation 1.7 and 0.85 ml of DIPEA in 10 ml of DCM is admixed at AT dropwise with 0.21 ml of 2-chloroacetyl chloride and left with stirring at AT for 30 minutes. The reaction mixture is washed with a pH=2 buffer solution, the organic phase is dried over $Na_2SO_4$ and the solvent is evaporated under vacuum. This gives 0.9 g of the expected product, which is used as it is.

Preparation 2.6

1-(2-Chloroacetyl)-4-[3-(trifluoromethyl)phenyl]-4-piperidinecarboxamide (IIa): $R_1$=3-$CF_3$; $R_2$=H; $R_3$=—$CONH_2$; Hal=Cl.

A mixture of 0.7 g of the compound obtained in preparation 1.8 and 0.37 ml of triethylamine in 10 ml of DCM and 10 ml of dioxane is admixed dropwise and at AT with 0.21 ml of 2-chloroacetyl chloride and is left with stirring at AT for 2 hours. It is concentrated under vacuum, the residue is taken up in water, and the precipitate formed is isolated with suction and dried. This gives 0.82 g of the expected product, m.p.=195-198° C.

Preparation 2.7

1-[4-Hydroxy-4-[3-(trifluoromethyl)phenyl]-1-piperidinyl]-2-propen-1-one (IIb): $R_1$=3-$CF_3$; $R_2$=H; $R_3$=—OH.

An ice bath is used to cool a mixture of 5 g of the compound obtained in preparation 1.1 and 8 ml of triethylamine in 50 ml of DCM which is then admixed dropwise with 2.07 ml of 3-bromopropionyl chloride and left with stirring for 2 hours, during which the temperature is allowed to return to AT. The reaction mixture is washed with saturated $K_2CO_3$ solution and with water, the organic phase is dried over $Na_2SO_4$ and the solvent is evaporated under vacuum. The residue is chromatographed on silica gel, eluting with a DCM/MeOH (98.5/1.5 to 97/3; v/v) mixture. This gives 4.6 g of the expected product, which is used as it is.

Example 1

Compound 1

4-[3-(Trifluoromethyl)phenyl]-1-[[4-[3-(trifluoromethyl)phenyl]piperazin-1-yl]acetyl]piperidin-4-ol hydrochloride (I), HCl: $R_1$ = 3-$CF_3$; $R_2$ = H; $R_3$ = —OH;

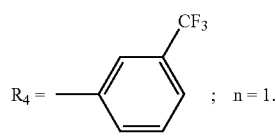
; n = 1.

A mixture of 0.8 g of the compound obtained in preparation 2.1, 0.6 g of 1-[3-(trifluoromethyl)phenyl]piperazine, 0.475 g of potassium iodide and 0.72 g of $K_2CO_3$ in 40 ml of acetonitrile is left with stirring at AT for 4 hours. Saturated $K_2CO_3$ solution is added to the reaction mixture, which is extracted with AcOEt, the organic phase is washed with water and with saturated NaCl solution and dried over $Na_2SO_4$ and the solvent is evaporated under vacuum. The residue is chromatographed on silica gel, eluting with a DCM/MeOH (96/4; v/v) mixture. The product obtained is taken up in 2N hydrochloric ether solution and, following trituration, the precipitate formed is filtered off with suction. This gives 1.13 g of the expected product, m.p.=130° C. (dec.).

Example 2

Compound 5

[[1-[(4-Phenylpiperazin-1-yl)acetyl]-4-[3-(trifluoromethyl)phenyl]piperidin-4-yl]methyl]amine hydrochloride (I), HCl: $R_1$ = 3-$CF_3$; $R_2$ = H; $R_3$ = —$CH_2NH_2$;

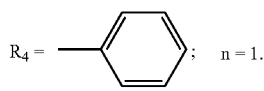
; n = 1.

A) tert-Butyl [[1-[(4-phenylpiperazin-1-yl)acetyl]-4-[3-(trifluoromethyl)phenyl]piperidin-4-yl]methyl]carbamate A mixture of 4.2 g of the compound obtained in preparation 2.2, 1.57 g of 1-phenylpiperazine, 1.6 g of potassium iodide and 2.67 g of $K_2CO_3$ in 40 ml of acetonitrile is left with stirring at AT overnight. The reaction mixture is concentrated under vacuum, the residue is taken up in water and extracted with ether, the organic phase is dried over $Na_2SO_4$ and the solvent is evaporated under vacuum. This gives 7 g of the expected product, which is used as it is.

B) [[1-[(4-phenylpiperazin-1-yl)acetyl]-4-[3-(trifluoromethyl)phenyl]piperidin-4-yl]methyl]amine hydrochloride A mixture of 7 g of the compound obtained in the preceding step, 100 ml of 2N hydrochloric ether and 50 ml of MeOH is left with stirring at AT for 30 minutes. 20 ml of 30% HCl solution are added and the mixture is left with stirring at AT for 1 hour. The reaction mixture is concentrated under vacuum, the residue is taken up in 10% NaOH solution and extracted with DCM, the organic phase is dried over $Na_2SO_4$ and the solvent is evaporated under vacuum. The residue is chromatographed on silica gel H, eluting with a DCM/MeOH/$H_2O$ (from 100/5/0.5 to 100/10/1; v/v/v) mixture. This gives 3.5 g of the expected product, in the form of the free base. 0.4 g of the product obtained is taken up in 2N hydrochloric ether solution, and left with stirring, and the precipitate formed is filtered off with suction. This gives 0.33 g of the expected product, m.p.=185-200° C.

Mass spectrum: $MH^+$=461.2.

Example 3

Compound 6

(2-Furylmethyl)[[1-[(4-phenylpiperazin-1-yl)acetyl]-4-[3-(trifluoromethyl)phenyl]piperidin-4-yl]methyl]amine $R_1$ = 3-$CF_3$; $R_2$ = H; $R_3$ = —$CH_2NHCH_2$— 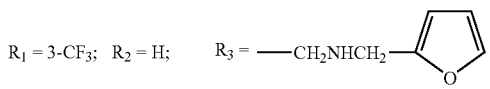

-continued

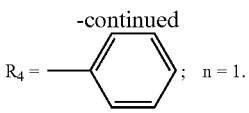

A mixture of 0.67 g of compound 5 in the form of free base, 0.14 g of 2-furaldehyde and 3 drops of acetic acid in 30 ml of THF is admixed in portions with 0.62 g of sodium triacetoxyborohydride and left with stirring at AT overnight. The reaction mixture is concentrated under vacuum, the residue is taken up in 10 ml of MeOH and the system is heated at 80° C. for 30 minutes. The mixture is concentrated under vacuum, the residue is taken up in 10% NaOH solution and extracted with DCM, the organic phase is dried over $Na_2SO_4$ and the solvent is evaporated under vacuum. The residue is chromatographed on silica gel H, eluting with a DCM/MeOH (from 100/1 to 100/5; v/v) mixture. This gives 0.24 g of the expected product, following recrystallization from iso ether; m.p.=119° C.

Mass spectrum: $MH^+$=541.2.

Example 4

Compound 11

N-Methyl-1-[1-[(4-phenylpiperazin-1-yl)acetyl]-4-[3-(trifluoromethyl)phenyl]piperidin-4-yl]methanamine dihydrochloride, $3H_2O$ (I), 2 HCl: $R_1$ = 3-$CF_3$; $R_2$ = H; $R_3$ = ——$CH_2NHCH_3$;

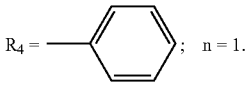

A) tert-Butylmethyl[[1-[(4-phenylpiperazin-1-yl)acetyl]-4-[3-(trifluoromethyl)phenyl]piperidin-4-yl]-methyl]carbamate A mixture of 1.98 g of the compound obtained in preparation 2.3, 0.74 g of 1-phenylpiperazine, 0.5 g of potassium iodide and 2.0 g of $K_2CO_3$ in 20 ml of acetonitrile is left with stirring at AT for 3 days. The reaction mixture is concentrated under vacuum, the residue is taken up in saturated $K_2CO_3$ solution and extracted with AcOEt, the organic phase is washed with water and dried over $Na_2SO_4$ and the solvent is evaporated under vacuum. The residue is chromatographed on silica gel, eluting with a DCM/MeOH (97/3; v/v) mixture. This gives 1.6 g of the expected product, which is used as it is.

B) N-Methyl-1-[1-[(4-phenylpiperazin-1-yl)acetyl]-4-[3-(trifluoromethyl)phenyl]piperid-4-yl]methanamine dihydrochloride, $3H_2O$ A solution of 1.6 g of the compound obtained in the preceding step in 10 ml of methanol is admixed with 1 drop of water and then, over 1 hour, with 50 ml of 2N hydrochloric ether solution and is left with stirring at AT for 24 hours. The precipitate formed is filtered off with suction and washed with ether. This gives 1.2 g of the expected product, m.p.=190-200° C.

Example 5

Compound 12

N,N-Dimethyl-1-[1-[(4-phenylpiperazin-1-yl)acetyl]-4-[3-(trifluoromethyl)phenyl]piperidin-4-yl]methanamine (I): $R_1$ = 3-$CF_3$; $R_2$ = H; $R_3$ = ——$CH_2N(CH_3)_2$;

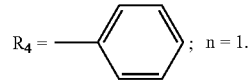

A suspension of 0.5 g of compound 11 in 20 ml of THF is admixed at AT with 0.5 ml of acetic acid and then with 0.14 ml of 37% aqueous formaldehyde solution and 0.36 g of sodium triacetoxyborohydride and is left with stirring at AT for 3 hours. The reaction mixture is concentrated under vacuum, the residue is taken up in saturated $K_2CO_3$ solution and extracted with AcOEt, the organic phase is washed with water and dried over $Na_2SO_4$ and the solvent is evaporated under vacuum. The residue is chromatographed on silica gel, eluting with a DCM/MeOH (95/5; v/v) mixture. This gives 0.25 g of the expected product, following recrystallization from DCM/iso ether; m.p.=123-124° C.

Compound 12 may also be prepared in accordance with the following procedure:

A solution of 0.53 g of 1-phenylpiperazine, 0.12 g of potassium iodide and 1.2 g of $K_2CO_3$ in 5 ml of acetonitrile is admixed with the solution of the compound of preparation 2.4 in ether and is left with stirring at AT overnight. The reaction mixture is concentrated under vacuum, the residue is taken up in saturated $K_2CO_3$ solution and extracted with AcOEt, the organic phase is washed with water and with saturated NaCl solution and dried over $Na_2SO_4$ and the solvent is evaporated under vacuum. The residue is chromatographed on silica gel, eluting with a DCM/MeOH (96/4; v/v) mixture. This gives 0.932 g of the expected product, following recrystallizatiion from a DCM/iso ether mixture; m.p.=122° C.

Example 6

Compound 13

N-Methyl-N-[[1-[(4-phenylpiperazin-1-yl)acetyl]-4-[3-(trifluoromethyl)phenyl]piperidin-4-yl]-methyl]ethanamine dihydrochloride, $3 H_2O$ (I), 2 HCl: $R_1$ = 3-$CF_3$; $R_2$ = H; $R_3$ = ——$CH_2N(CH_3)CH_2CH_3$;

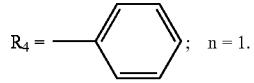

A suspension of 0.5 g of compound 11 and 0.5 ml of acetic acid in 10 ml of THF is admixed at AT with 0.1 ml of acetaldehyde and then, in one go, with 0.36 g of sodium triacetoxyborohydride and is left with stirring at AT for 24 hours. The reaction mixture is concentrated under vacuum, the residue is taken up in 20 ml of MeOH and the system is heated at 65° C. for 3 hours. The mixture is concentrated under vacuum, the residue is taken up in saturated $K_2CO_3$ solution and extracted with AcOEt, the organic phase is washed with water and dried over $Na_2SO_4$ and the solvent is evaporated under vacuum. The residue is chromatographed on silica gel, eluting with a DCM/MeOH (96/4; v/v) mixture. The product obtained is dissolved in 10 ml of ether and 1 drop of MeOH, 2N hydrochloric ether solution is added and the precipitate formed is filtered off with suction. This gives 0.18 g of the expected product.

Mass spectrum: $MH^+$=503.4.

Example 7

Compound 20

[[1-[[4-(3,4-Dimethoxyphenyl)piperazin-1-yl]acetyl]-4-[3-(trifluoromethyl)phenyl]piperidin-4-yl]methyl]dimethylamine trihydrochloride, 2 $H_2O$ (I), 3 HCl: $R_1$ = 3-$CF_3$; $R_2$ = H; $R_3$ = ——$CH_2N(CH_3)_2$;

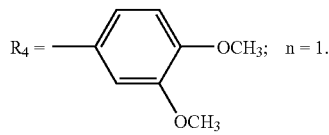; n = 1.

A solution of 0.65 g of compound 19 and 0.5 ml of acetic acid in 10 ml of THF is admixed with 0.5 ml of 37% aqueous formaldehyde solution and then in one go with 1.25 g of sodium triacetoxyborohydride and is left with stirring at AT overnight. Then 0.25 ml of acetic acid, 0.25 ml of 37% aqueous formaldehyde solution and 0.55 g of sodium triacetoxyborohydride are added and the mixture is left with stirring at AT for 24 hours. It is concentrated under vacuum, the residue is taken up in 40 ml of MeOH and the system is heated at 65° C. for 5 hours. The mixture is concentrated under vacuum, the residue is taken up in saturated $K_2CO_3$ solution and extracted with AcOEt, the organic phase is washed with water and dried over $Na_2SO_4$ and the solvent is evaporated under vacuum. The residue is chromatographed on alumina, eluting with a DCM/MeOH (98/2; v/v) mixture. The product obtained is taken up in 2N hydrochloric ether solution and left with stirring and the precipitate formed is filtered off with suction. This gives 0.33 g of the expected product, m.p.=190-210° C.

Example 8

Compound 21

N-Ethyl-N-[[1-[[4-(3-methoxyphenyl)piperazin-1-yl]acetyl]-4-[3-(trifluoromethyl)phenyl]piperidin-4-yl]methyl]ethanamine dihydrochloride (I), 2 HCl: $R_1$ = 3-$CF_3$; $R_2$ = H; $R_3$ = ——$CH_2N(CH_2CH_3)_2$;

-continued

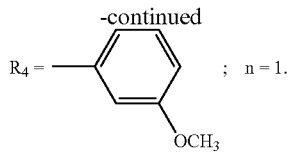; n = 1.

A suspension of 0.5 g of compound 15 and 0.5 ml of acetic acid in 8 ml of THF is admixed at AT with 0.15 ml of acetaldehyde and then with 0.56 g of sodium triacetoxyborohydride and is left with stirring at AT for 24 hours. The reaction mixture is concentrated under vacuum, the residue is taken up in 30 ml of MeOH and the system is heated at 65° C. for 3 hours. It is concentrated under vacuum, the residue is taken up in saturated $K_2CO_3$ solution and extracted with AcOEt, the organic phase is washed with water and dried over $Na_2SO_4$ and the solvent is evaporated under vacuum. The residue is chromatographed on silica gel, eluting with the DCM/MeOH (97/3; v/v) mixture. The product obtained is taken up in 2N hydrochloric ether solution and left with stirring and the precipitate formed is filtered off with suction. This gives 0.14 g of the expected product.

Mass spectrum: $MH^+$=547.2.

Example 9

Compound 22

1-[2-[4-(Azetidin-1-ylcarbonyl)-4-[3-(trifluoromethyl)phenyl]piperidin-1-yl]-2-oxoethyl]-4-phenylpiperazine

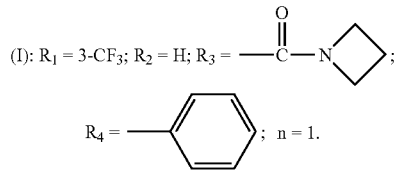

A mixture of 0.42 g of the compound obtained in preparation 2.5, 0.2 g of 1-phenylpiperazine, 0.2 g of potassium iodide and 0.3 g of $K_2CO_3$ in 10 ml of acetonitrile is left with stirring at AT for 2 hours. Saturated $K_2CO_3$ solution is added to the reaction mixture, which is extracted with DCM, the organic phase is washed with water and dried over $Na_2SO_4$ and the solvent is evaporated under vacuum. The residue is chromatographed on silica gel, eluting with a DCM/MeOH (97/3; v/v) mixture. This gives 0.25 g of the expected product, following recrystallization from a DCM/iso ether mixture; m.p.=147-149° C.

Mass spectrum: $MH^+$=515.6.

The table below illustrates the chemical structures and physical properties of some examples of compounds according to the invention. In this table:

- in the "salt" column, "-" represents a compound in the free base form, while "HCl" represents a compound in hydrochloride form and "$C_2H_2O_4$" represents a compound in the oxalate form.

TABLE I (I)

[Structure: substituted phenyl (positions 1-6 with R1 at 3, R2 at 5, R3 at 1) connected to a 4-substituted piperidine, N-C(=O)-(CH2)n-N-piperazine-N-R4]

| Compounds | R₁ | R₂ | R₃ | n | R₄ | Salt; hydrate | m.p. °C.; crystallization solvent; MH⁺ |
|---|---|---|---|---|---|---|---|
| 1 | 3-CF₃ | H | —OH | 1 | 3-CF₃-phenyl | HCl; 1 H₂O | 130; ether; — |
| 2 (a) | 3-CF₃ | H | —OH | 1 | 3,4-di-CH₃-phenyl | C₂H₂O₄ | 193-196; ether; — |
| 3 (a) | 3-CF₃ | H | —OH | 1 | 3,5-di-Cl-phenyl | — | —; —; 516 |
| 4 (a) | 3-CF₃ | H | —OH | 1 | 4-CH₃-phenyl | — | —; —; 462 |
| 5 | 3-CF₃ | H | —CH₂NH₂ | 1 | phenyl | 3 HCl; 1.5 H₂O | 185-200; ether; 461.2 |
| 6 | 3-CF₃ | H | —CH₂NHCH₂-(2-furyl) | 1 | phenyl | — | 119; iso ether; 541.2 |
| 7 (b) | 3-CF₃ | H | —CH₂NHCH₂-(2-thienyl) | 1 | phenyl | — | 141; ether; 557.2 |
| 8 (b) | 3-CF₃ | H | —CH₂NHCH₂-(2-pyridyl) | 1 | phenyl | C₂H₂O₄; 0.5 H₂O | 152-160; ether; 552.4 |
| 9 (b) | 3-CF₃ | H | —CH₂NHCH₂-(3-pyridyl) | 1 | phenyl | 2 C₂H₂O₄; 0.5 H₂O | 85-100; ether; 552.7 |
| 10 (b) | 3-CF₃ | H | —CH₂NHCH₂-(4-pyridyl) | 1 | phenyl | C₂H₂O₄ | 108-118; ether; 552.4 |
| 11 | 3-CF₃ | H | —CH₂NHCH₃ | 1 | phenyl | 2 HCl; 3 H₂O | 190-200; MeOH/ether; — |

TABLE I-continued $$(I)$$

[Structure: Phenyl ring with R1 at position 3, R2 at position 5, R3 at position 1 (attached to piperidine), connected to piperidine-N-C(=O)-(CH2)n-N-piperazine-N-R4. Positions labeled 1-6 on phenyl.]

| Compounds | R₁ | R₂ | R₃ | n | R₄ | Salt; hydrate | m.p. °C.; crystallization solvent; MH⁺ |
|---|---|---|---|---|---|---|---|
| 12 | 3-CF₃ | H | —CH₂N(CH₃)₂ | 1 | phenyl | — | 122; DCM/iso ether; 489.4 |
| 13 | 3-CF₃ | H | —CH₂N(CH₃)—CH₂CH₃ | 1 | phenyl | 2 HCl; 3 H₂O | —; ether; 503.4 |
| 14 (c) | 3-CF₃ | H | —CH₂NH₂ | 1 | 4-F-phenyl | 3 HCl; 2 H₂O | —; ether; 479.2 |
| 15 (c) | 3-CF₃ | H | —CH₂NH₂ | 1 | 3-OCH₃-phenyl | 2 HCl; 3 H₂O | —; MeOH/ether; 491.4 |
| 16 (c) | 3-CF₃ | H | —CH₂NH₂ | 1 | 3,4-diCl-phenyl | — | 109-110; DCM/iso ether; — |
| 17 (d) | 3-CF₃ | H | —CH₂NHCH₃ | 1 | 2,4-diCH₃-phenyl | 2 HCl; 3 H₂O | 204-211; ether; 503.7 |
| 18 (e) | 3-CF₃ | H | —CH₂N(CH₃)₂ | 1 | 2,4-diCH₃-phenyl | 2 HCl; 5 H₂O | —; ether; 517.4 |
| 19 (c) | 3-CF₃ | H | —CH₂NH₂ | 1 | 3,4-diOCH₃-phenyl | 3 HCl; 2 H₂O | 208; MeOH/ether; 521.5 |
| 20 | 3-CF₃ | H | —CH₂N(CH₃)₂ | 1 | 3,4-diOCH₃-phenyl | 3 HCl; 2 H₂O | 190-210; ether; — |
| 21 | 3-CF₃ | H | —CH₂N(CH₂CH₃)₂ | 1 | 3-OCH₃-phenyl | 2 HCl; 3.5 H₂O | —; ether; 547.2 |

TABLE I-continued
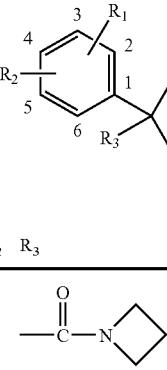
(I)
| Compounds | R₁ | R₂ | R₃ | n | R₄ | Salt; hydrate | m.p. °C.; crystallization solvent; MH⁺ |
|---|---|---|---|---|---|---|---|
| 22 | 3-CF₃ | H | 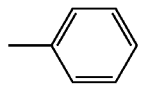 | 1 | 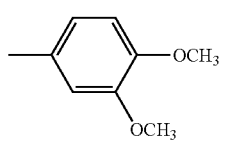 | — | 147-149; DCM/iso ether; 515.6 |
| 23 | 3-CF₃ | H | —CH₂NHCH₃ | 1 | 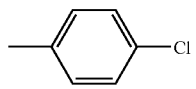 | 2 HCl; 3 H₂O | —<br>ether; 535.2 |
| 24 (a) | 3-CF₃ | H | —OH | 1 | 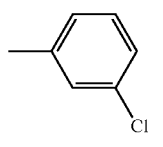 | — | —<br>482.1 |
| 25 (a) | 3-CF₃ | H | —OH | 1 | 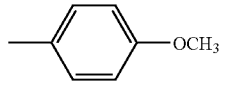 | — | —<br>482.1 |
| 26 (a) | 3-CF₃ | H | —OH | 1 | 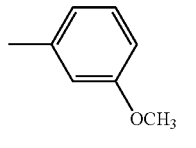 | — | —<br>478.2 |
| 27 (a) | 3-CF₃ | H | —OH | 1 | 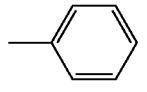 | — | —<br>478.2 |
| 28 (f) | 3-CF₃ | H | —CONH₂ | 1 | 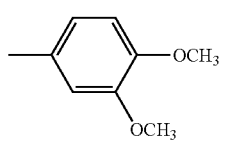 | — | —<br>474.8 |
| 29 (f) | 3-CF₃ | H | —CONH₂ | 1 | 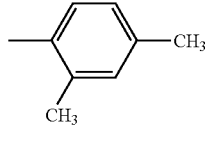 | — | —<br>502.8 |
| 30 (f) | 3-CF₃ | H | —CONH₂ | 1 | 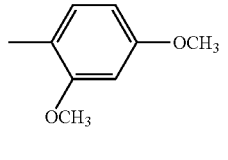 | — | —<br>534.8 |
| 31 (f) | 3-CF₃ | H | —CONH₂ | 1 | 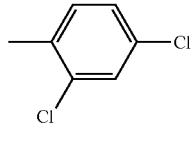 | — | —<br>542.7 |

TABLE I-continued (I)

[Structure: phenyl ring (positions labeled 3-R₁, 4, 5-R₂, 6, 1, 2, with R₃ at position connecting to piperidine) attached to a 4-substituted piperidine N-C(=O)-(CH₂)ₙ-N-piperazine-N-R₄]

| Compounds | R₁ | R₂ | R₃ | n | R₄ | Salt; hydrate | m.p. °C.; crystallization solvent; MH⁺ |
|---|---|---|---|---|---|---|---|
| 32 (g) | 3-CF₃ | H | —OH | 2 | phenyl | — | —<br>—<br>461.8 |
| 33 (g) | 3-CF₃ | H | —OH | 2 | 4-CH₃-phenyl | — | —<br>—<br>475.8 |
| 34 (g) | 3-CF₃ | H | —OH | 2 | 4-F-phenyl | — | —<br>—<br>479.7 |
| 35 (g) | 3-CF₃ | H | —OH | 2 | 4-OCH₃-phenyl | — | —<br>—<br>491.8 |
| 36 (h) | 3-CF₃ | H | —CH₂N(CH₃)CH₂-(2-furyl) | 1 | 3,4-di-OCH₃-phenyl | 3 HCl, 2 H₂O | —<br>—<br>615 |
| 37 (b) | 3-CF₃ | H | —CH₂NHCH₂-(2-furyl) | 1 | phenyl | — | 137;<br>iso ether;<br>541.2 |
| 38 (c) | 3-CF₃ | H | —CH₂NH₂ | 1 | 2,6-di-CH₃-phenyl | — | 114-116;<br>DCM/iso ether;<br>489.6 |

(a) Compound prepared by the procedure described in Example 1, from the compound of preparation 2.1 and the corresponding compound of formula (III).

(b) Compound prepared by the procedure described in Example 3, from Compound 5 and the corresponding compound of formula (IV).

(c) Compound prepared by the procedures described in steps A and B of Example 2, from the compound obtained in preparation 2.2 and the corresponding compound of formula (III).

(d) Compound prepared by the procedures described in steps A and B of Example 4, from the compound obtained in preparation 2.3 and the corresponding compound of formula (III).

(e) Compound prepared by the procedure described in Example 5, from the corresponding compound of formula (I) in which R₃ = CH₂NHCH₃.

(f) Compound prepared by the procedure described in Example 1, from the compound obtained in preparation 2.6 and the corresponding compound of formula (III).

(g) Compound prepared by the procedure described in Example 1, from the compound obtained in preparation 2.7 and the corresponding compound of formula (III).

(h) Compound prepared by the procedure described in Example 3, from Compound 23 and the corresponding compound of formula (IV).

The compounds according to the invention were subjected to biochemical studies.

Cell Culture:

The SH-SY-5Y strain (human neuroblastoma) is cultured conventionally in a DMEM culture medium (Dulbecco's Modified Eagle's Medium) (Gibco BRL, France) containing FCS (5%) (foetal calf serum) (Boehringer Mannheim, Germany), sodium pyruvate (1 mM), anti-PPLO (5 ml) (antimycoplasma agent: Tylocine® prepared in a normal saline solution, 6000 µg/ml), gentamycin (0.1 mg/ml) and glutamine (4 mM) in collagen-coated culture flasks (Becton Dickinson, France).

The stock strain SK-N-BE (human neuroblastoma) and the clone Bep 75 expressing the human $p75^{NTR}$ receptor (SK-N-BE Bep 75) are conventionally cultured in a DMEM culture medium containing FCS (5%), sodium pyruvate (1 mM), anti-PPLO (5 ml), gentamycin (0.1 mg/ml) and glutamine (4 mM).

Study of the Binding of $^{125}$I-NGF to the $p75^{NTR}$ Receptor

The study of the binding of $^{125}$I-NGF (neuronal growth factor radiolabelled with iodine-125) is carried out on a cellular suspension of the two strains SH-SY-5Y and SK-N-BE Bep 75 in accordance with the method described by Weskamp (Neuron, 1991, 6, 649-663). Nonspecific binding is determined by measuring the total binding after one hour of preincubation with the cells at 37° C. in the presence of nonradiolabelled NGF (1 µM). The specific binding is calculated by the difference between the measurement of total binding and the measurement of nonspecific binding. The competition experiments are carried out using a $^{125}$I-NGF concentration of 0.3 nM. The concentrations inhibiting by 50% ($IC_{50}$) the binding of $^{125}$I-NGF to the $p75^{NTR}$ receptor of the compounds according to the invention are low and vary from $10^{-6}$ to $10^{-11}$ M.

Measurement of Apoptosis:

The cells (human neuroblastoma strains SH-SY-5Y and SK-N-BE Bep 75) are established in Petri dishes 35 mm in diameter (Biocoat collagen I) ($10^5$ cells/well) in a DMEM culture medium containing 5% FCS for 24 h. The culture medium is then removed, the cells are rinsed with PBS (Dulbecco's phosphate buffered saline) and either fresh medium containing 5% FCS or medium containing NGF at the concentration of 10 ng/ml is added in the presence or absence of the compounds according to the invention. The levels of apoptosis are measured 48 hours after the treatments in the case of the strain SH-SY-5Y and 24 hours later in the case of the strain SK-N-BE Bep 75 by quantifying the cytoplasmic histones associated with the DNA fragments (cell death detection ELISA, Boehringer Mannheim, Germany). The levels of apoptosis are expressed as quantity of oligonucleosomes/105 cells±SD. Each value corresponds to the mean of 9 experimental points distributed over 3 independent experiments. The compounds of formula (I) exhibit NGF-induced apoptosis inhibitory activity with $IC_{50}$ values varying from $10^{-6}$ to $10^{-11}$ M.

Thus the binding of the compounds according to the invention to the $p75^{NTR}$ receptor results, on the one hand, at the biochemical level, in the inhibition of the dimerization of the receptor induced by neurotrophins, and, on the other hand, at the cellular level, in the inhibition of the proapoptotic effect mediated by the $p75^{NTR}$ receptor.

The compounds according to the invention can therefore be used for the preparation of medicaments, in particular of medicaments intended for the prevention or treatment of any pathology where the $p75^{NTR}$ receptor is involved.

Thus, in another of its aspects, the invention provides medicaments comprising a compound of formula (I), or an addition salt thereof with a pharmaceutically acceptable acid, or alternatively a solvate or a hydrate of the compound of formula (I).

Thus the compounds according to the invention may be used, in humans or in animals, in the treatment or prevention of various $p75^{NTR}$-dependent conditions such as central and peripheral neurodegenerative diseases such as senile dementia, epilepsy, Alzheimer's disease, Parkinson's disease, Huntington's chorea, Down's syndrome, prion diseases, amnesia, schizophrenia; amyotrophic lateral sclerosis, multiple sclerosis; cardiovascular conditions such as post-ischaemic cardiac damage, cardiomyopathies, myocardial infarction, cardiac insufficiency, cardiac ischaemia, cerebral infarction; peripheral neuropathies (of diabetic, traumatic or iatrogenic origin); damage to the optic nerve and to the retina; spinal cord trauma and cranial trauma; atherosclerosis; stenoses; cicatrization; alopecia.

The compounds according to the invention may also be used in the treatment of cancers such as that of the lung, of the thyroid, of the pancreas, of the prostate, of the small intestine and of the colon, of the breast, in the treatment of tumours, of metastases and of leukaemias.

The compounds according to the invention may also be used in the treatment of chronic neuropathic and inflammatory pain and in the treatment of autoimmune diseases such as rheumatoid arthritis.

The compounds according to the invention may also be used in the treatment of bone fractures and in the treatment or prevention of bone diseases such as osteoporosis.

In another of its aspects, the present invention relates to pharmaceutical compositions comprising, as active principle, a compound according to the invention. These pharmaceutical compositions contain an effective dose of at least one compound according to the invention, or a pharmaceutically acceptable salt, a solvate or a hydrate of the said compound, and at least one pharmaceutically acceptable excipient.

The said excipients are selected, according to the pharmaceutical form and the desired mode of administration, from the customary excipients which are known to the person skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or its salt, solvate or hydrate where appropriate, may be administered in unit form for administration, as a mixture with conventional pharmaceutical excipients, to animals and to human beings for the prophylaxis or treatment of the above disorders or diseases.

The appropriate unit forms for administration comprise the forms for oral administration such as tablets, soft or hard gelatin capsules, powders, granules and oral solutions or suspensions, forms for sublingual, buccal, intratracheal, intraocular or intranasal administration, forms for administration by inhalation, forms for topical, transdermal, subcutaneous, intramuscular or intravenous administration, forms for rectal administration and implants. For topical application, the compounds according to the invention may be used in creams, gels, ointments or lotions.

By way of example, a unit form for administration of a compound according to the invention in tablet form may comprise the following components:

| | |
|---|---|
| Compound of the invention | 50.0 mg |
| Mannitol | 223.75 mg |
| Croscaramellose sodium | 6.0 mg |
| Cornstarch | 15.0 mg |
| Hydroxypropylmethylcellulose | 2.25 mg |
| Magnesium stearate | 3.0 mg |

For oral administration, the dose of active principle administered per day may be up to 0.01 to 100 mg/kg, in single or divided doses, preferably 0.02 to 50 mg/kg.

There may be particular cases in which higher or lower dosages are appropriate; such dosages are not outside the scope of the invention. According to the customary practice, the dosage appropriate for each patient is determined by the doctor according to the mode of administration, the weight and the response of the said patient.

The present invention, in another of its aspects, also relates to a method of treating the pathologies indicated above which comprises the administration, to a patient, of an effective dose of a compound according to the invention, or one of its pharmaceutically acceptable salts or its hydrates or solvates.

We claim:

1. A compound of formula (I):

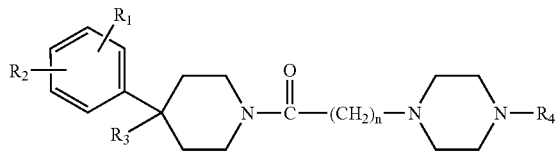

(I)

wherein:

n is 1 or 2;
$R_1$ is halogen, trifluoromethyl, $(C_1$-$C_4)$alkyl, $(C_1$-$C_4)$alkoxy or trifluoromethoxy;
$R_2$ is hydrogen or halogen;
$R_3$ is hydrogen, —$OR_5$, —$CH_2OR_5$, —$NR_6R_7$, —$NR_8COR_9$, —$CH_2NR_{10}R_{11}$, $(C_1$-$C_4)$alkoxycarbonyl, —$CONR_{12}R_{13}$ or —CN;
$R_4$ is phenyl which is unsubstituted or mono-, di- or trisubstituted by a substituent selected independently from halogen, $(C_1$-$C_4)$alkyl, $(C_1$-$C_4$alkoxy, or trifluoromethyl;
$R_5$ is hydrogen or $(C_1$-$C_4)$alkyl;
$R_6$ and $R_7$ are each independently hydrogen or $(C_1$-$C_4)$alkyl;
$R_8$ is hydrogen or $(C_1$-$C_4)$alkyl;
$R_9$ is $(C_1$-$C_4)$alkyl;
$R_{10}$ is hydrogen or $(C_1$-$C_4)$alkyl,
$R_{11}$ is hydrogen, $(C_1$-$C_4)$alkyl or —$CH_2R_{14}$, or
$R_{10}$ and $R_{11}$ taken together with the nitrogen atom to which they are attached form a heterocycle selected from aziridine, azetidine, pyrrolidine, piperidine or morpholine;
$R_{12}$ and $R_{13}$ are each independently hydrogen or $(C_1$-$C_4)$alkyl, or
$R_{12}$ and $R_{13}$ taken together with the nitrogen atom to which they are attached form a heterocycle selected from azetidine, pyrrolidine, piperidine, morpholine or piperazine which is unsubstituted or substituted in position 4 by a $(C_1$-$C_4)$alkyl;

$R_{14}$ is an aromatic group selected from:

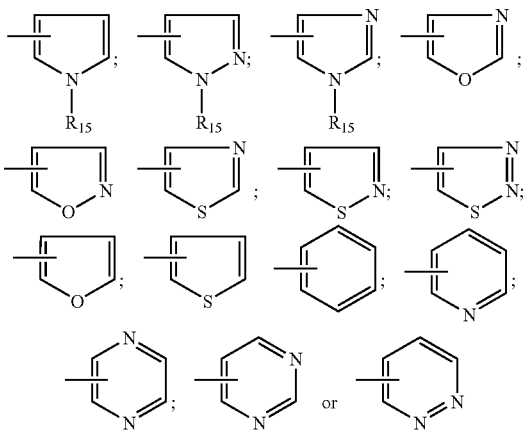

wherein the aromatic group is unsubstituted, monosubstituted or disubstituted by a substituent selected independently from halogen, $(C_1$-$C_3)$alkyl or $(C_1$-$C_3)$alkoxy; and
$R_{15}$ is hydrogen or $(C_1$-$C_3)$alkyl;
or an addition salt with an acid thereof, or a hydrate thereof.

2. The compound according to claim 1, characterized wherein:
n is 1 or 2;
or an addition salt with an acid thereof, or a hydrate thereof.

3. The compound according to claim 1, wherein:
$R_1$ is in position 3 of the phenyl and is trifluoromethyl;
or an addition salt with an acid thereof, or a hydrate thereof.

4. The compound according to claim 1, wherein:
$R_2$ is hydrogen;
or an addition salt with an acid thereof, or a hydrate thereof.

5. The compound according to claim 1, wherein:
$R_3$ is hydroxy, aminomethyl, (2-furylmethylamino)methyl, (2-thienylmethylamino)methyl, (2-pyridylmethylamino)methyl, (3-pyridylmethylamino)methyl, (4-pyridylmethylamino)methyl, (methyl-amino)methyl, (dimethylamino)methyl, (N-methylethylamino)methyl, (diethylamino)methyl, azetidin-1-ylcarbonyl, aminocarbonyl, (N-methyl-2-furylmethylamino)methyl or (3-furylmethylamino)methyl,
or an addition salt with an acid thereof, or a hydrate thereof.

6. The compound according to claim 1, wherein:
$R_4$ is phenyl, 4-chlorophenyl, 3-chlorophenyl, 4-fluorophenyl, 2,4-dichlorophenyl, 3,4-dichlorophenyl, 3,5-dichlorophenyl, 4-methylphenyl, 2,4-dimethylphenyl, 3,4-dimethylphenyl, 3-methoxyphenyl, 4-methoxyphenyl, 2,4-dimethoxyphenyl, 3,4-dimethoxyphenyl, 3-(trifluoromethyl)phenyl or 2,3-dimethylphenyl,
or an addition salt with an acid thereof, or a hydrate thereof.

7. The compound according to claim 1, wherein:
n is 1 or 2;
$R_1$ is in position 3 of the phenyl and is trifluoromethyl;
$R_2$ is hydrogen;
$R_3$ is hydroxy, aminomethyl, (2-furylmethylamino)methyl, (2-thienylmethylamino)methyl, (2-pyridylmethylamino)methyl, (3-pyridylmethylamino)methyl, (4-pyridylmethylamino)methyl, (methyl-amino)methyl, (dimethylamino)methyl, (N-methylethylamino)methyl, (diethylamino)methyl, azetidin-1-ylcarbonyl, aminocarbonyl, (N-methyl-2-furylmethylamino)methyl, or (3-furylmethylamino)methyl;

R$_4$ is phenyl, 4-chlorophenyl, 3-chlorophenyl, 4-fluorophenyl, 2,4-dichlorophenyl, 3,4-dichlorophenyl, 3,5-dichlorophenyl, 4-methylphenyl, 2,4-dimethylphenyl, 3,4-dimethylphenyl, 3-methoxyphenyl, 4-methoxyphenyl, 2,4-dimethoxyphenyl, 3,4-dimethoxyphenyl, 3-(trifluoromethyl)phenyl or 2,3-dimethylphenyl;

or an addition salt with an acid thereof, or a hydrate thereof.

8. A process for preparing the compound according to claim 1 wherein n=1, comprising:

a1) reacting a compound of formula (IIa)

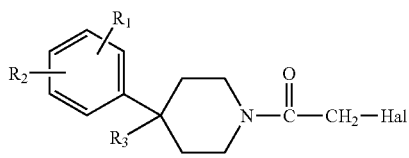
(IIa)

wherein R$_1$, R$_2$ and R$_3$ are as defined in claim 1 and Hal is halogen, provided that when R$_3$ contains a hydroxy or amine group, then the hydroxy or amine group may be protected, with a compound of formula (III)

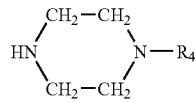
(III)

wherein R$_4$ is as defined in claim 1; and b1) deprotecting the hydroxy or amine group present in R$_3$ where appropriate.

9. The process according to claim 8, wherein Hal is chlorine or bromine.

10. A process for preparing the compound according to claim 1 wherein n=2, comprising:

a2) reacting a compound of formula (IIb)

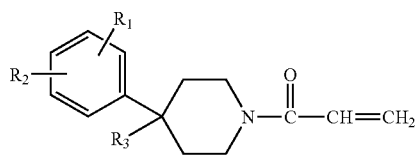
(IIb)

wherein R$_1$, R$_2$ and R$_3$ are as defined in claim 1, provided that when R$_3$ contains a hydroxy or amine group, then the hydroxy or amine group may be protected, with a compound of formula (III)

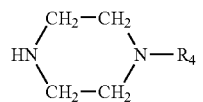
(III)

wherein R$_4$ is as defined in claim 1; and b2) deprotecting the hydroxy or amine group present in R$_3$ where appropriate.

11. A process for preparing the compound according to claim 1 wherein R$_3$ is —CH$_2$NR$_{10}$R$_{11}$, and R$_{10}$ and R$_{11}$ are hydrogen, comprising:

a3) reacting a compound of formula (IIc) or (IId)

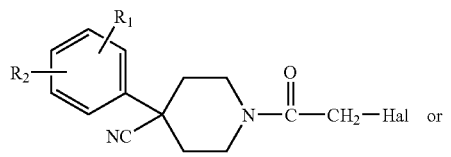
(IIc)

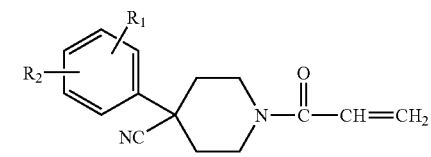
(IId)

wherein R$_1$ and R$_2$ are as defined in claim 1 and Hal is halogen, with a compound of formula (III)

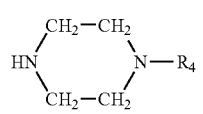
(III)

wherein R$_4$ is as defined claim 1 to give a compound of formula (I), wherein R$_3$ is —CN, and

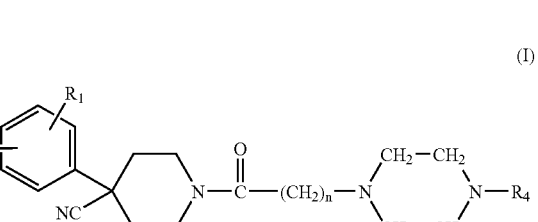
(I)

R$_3$ = —CN b3) reducing the compound of formula (I), wherein $R_3$ is —CN, to give a compound of formula (I) wherein $R_3$=$CH_2NH_2$.

12. The process according to claim 11, wherein Hal is chlorine or bromine.

13. A process for preparing the compound according to claim 1 wherein $R_3$ is —$CH_2NR_{10}R_{11}$ and $R_{11}$ is —$CH_2R_{14}$, comprising a4) reacting a compound of formula (I), wherein $R_3$ is —$CH_2NHR_{10}$,

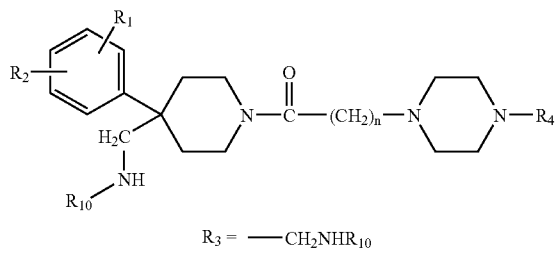

(I)

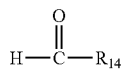 $R_3$ = —$CH_2NHR_{10}$ and $R_1$, $R_2$, $R_4$, $R_{10}$ and n are as defined in claim 1, with a compound of formula (IV):

$$H-\overset{O}{\underset{\|}{C}}-R_{14}$$

(IV)

wherein $R_{14}$ is as defined in claim 1, in the presence of an acid and in a solvent to give an iminium salt intermediate, and then reducing the iminium salt by a reducing agent.

14. A pharmaceutical composition comprising the compound according to claim 1, or a pharmaceutically acceptable salt or hydrate thereof, and at least one pharmaceutically acceptable excipient.

15. A pharmaceutical composition comprising the compound according to claim 2, or a pharmaceutically acceptable salt or hydrate thereof, and at least one pharmaceutically acceptable excipient.

16. A pharmaceutical composition comprising the compound according to claim 3, or a pharmaceutically acceptable salt or hydrate thereof, and at least one pharmaceutically acceptable excipient.

17. A pharmaceutical composition comprising the compound according to claim 4, or a pharmaceutically acceptable salt or hydrate thereof, and at least one pharmaceutically acceptable excipient.

18. A pharmaceutical composition comprising the compound according to claim 5, or a pharmaceutically acceptable salt or hydrate thereof, and at least one pharmaceutically acceptable excipient.

19. A pharmaceutical composition comprising the compound according to claim 6, or a pharmaceutically acceptable salt or hydrate thereof, and at least one pharmaceutically acceptable excipient.

20. A pharmaceutical composition comprising the compound according to claim 7, or a pharmaceutically acceptable salt or hydrate thereof, and at least one pharmaceutically acceptable excipient.

\* \* \* \* \*